US009290453B2

(12) United States Patent
Boyce et al.

(10) Patent No.: US 9,290,453 B2
(45) Date of Patent: Mar. 22, 2016

(54) QUINOLINES AND AZA-QUINOLINES AS CRTH$_2$ RECEPTOR MODULATORS

(75) Inventors: Christopher W. Boyce, Flemington, NJ (US); Salem Fevrier, Cranford, NJ (US); Kevin D. McCormick, Basking Ridge, NJ (US); Anandan Palani, Bridgewater, NJ (US); Robert G. Aslanian, Rockaway, NJ (US); Phieng Siliphaivanh, Newton, MA (US); Joey L. Methot, Westwood, MA (US); William Colby Brown, Cleveland Heights, OH (US); Henry Vaccaro, South Plainfield, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 407 days.

(21) Appl. No.: 13/996,371

(22) PCT Filed: Dec. 19, 2011

(86) PCT No.: PCT/US2011/065730
§ 371 (c)(1),
(2), (4) Date: Jun. 20, 2013

(87) PCT Pub. No.: WO2012/087872
PCT Pub. Date: Jun. 28, 2012

(65) Prior Publication Data
US 2013/0296300 A1 Nov. 7, 2013

Related U.S. Application Data

(60) Provisional application No. 61/426,832, filed on Dec. 23, 2010.

(51) Int. Cl.
| | |
|---|---|
| *A61K 31/47* | (2006.01) |
| *A61K 31/4709* | (2006.01) |
| *A61K 31/496* | (2006.01) |
| *A61K 31/4375* | (2006.01) |
| *C07D 215/48* | (2006.01) |
| *C07D 401/06* | (2006.01) |
| *C07D 401/12* | (2006.01) |
| *C07D 401/14* | (2006.01) |
| *C07D 471/04* | (2006.01) |
| *C07D 491/107* | (2006.01) |
| *C07D 405/12* | (2006.01) |
| *A61K 45/06* | (2006.01) |

(52) U.S. Cl.
CPC .......... *C07D 215/48* (2013.01); *A61K 31/4375* (2013.01); *A61K 31/47* (2013.01); *A61K 31/4709* (2013.01); *A61K 31/496* (2013.01); *A61K 45/06* (2013.01); *C07D 401/06* (2013.01); *C07D 401/12* (2013.01); *C07D 401/14* (2013.01); *C07D 405/12* (2013.01); *C07D 471/04* (2013.01); *C07D 491/107* (2013.01)

(58) Field of Classification Search
None
See application file for complete search history.

(56) References Cited

U.S. PATENT DOCUMENTS

| | | | |
|---|---|---|---|
| 5,434,155 A | 7/1995 | Fukazawa et al. | |
| 7,666,878 B2 | 2/2010 | Bala et al. | |
| 7,696,222 B2 | 4/2010 | Wang | |
| 8,394,819 B2 | 3/2013 | Berthelette et al. | |
| 8,546,422 B2 | 10/2013 | Leblanc et al. | |
| 8,592,383 B2 | 11/2013 | Huang et al. | |
| 8,637,541 B2 | 1/2014 | Wang | |
| 8,637,671 B2 | 1/2014 | Colucci et al. | |
| 8,927,559 B2 | 1/2015 | Aslanian et al. | |
| 2003/0055071 A1 | 3/2003 | Anthony et al. | |
| 2005/0038076 A1 | 2/2005 | Garst et al. | |
| 2010/0144786 A1 | 6/2010 | Cramp et al. | |
| 2013/0210805 A1 | 8/2013 | Aslanian et al. | |
| 2013/0303517 A1 | 11/2013 | Boyce et al. | |

FOREIGN PATENT DOCUMENTS

| | | |
|---|---|---|
| WO | 02/26713 A1 | 4/2002 |
| WO | 2004/009583 A2 | 1/2004 |
| WO | 2006/103120 A2 | 10/2006 |
| WO | 2007/071055 A1 | 6/2007 |
| WO | 2007/103905 A2 | 9/2007 |
| WO | 2007/138112 A2 | 12/2007 |
| WO | 2011/028947 A2 | 3/2011 |
| WO | WO2014055311 A1 | 4/2014 |

OTHER PUBLICATIONS

Ulven, T., et al., "Novel CRTH2 Antagonists: a review of patents from 2006 to 2009," Expert Opinion on Therapeutic Patents, Nov. 2010, vol. 20, Issue 11, pp. 1505-1530.
Hata, et al., "Structural determinants of arylacetic acid nonsteriodal anti-inflammatory drugs necessary for binding and activation of the prostaglandin D-2 receptor CRTH2," Molecular Pharmacology, Mar. 2005, vol. 67, Issue 3, pp. 640-647.
International Search Report & Written Opinion for PCT/US2011/65730 dated Apr. 19, 2012.

*Primary Examiner* — Emily Bernhardt
(74) *Attorney, Agent, or Firm* — Eric A. Meade; Catherine D. Fitch

(57) ABSTRACT

The invention provides certain quinolines and aza-quinolines of the Formula (I), and their pharmaceutically acceptable salts, wherein E, $J^1$, $J^a$, $J^b$, $R^2$, $R^3$, $R^{22}$, $R^a$, $R^b$, $R^c$, $R^d$, X, Y, b, n, and q are as defined herein. The invention also provides pharmaceutical compositions comprising such compounds, and methods of using the compounds for treating diseases or conditions associated with uncontrolled or inappropriate stimulation of CRTH$_2$ function.

12 Claims, No Drawings

QUINOLINES AND AZA-QUINOLINES AS CRTH$_2$ RECEPTOR MODULATORS

CROSS-REFERENCE TO RELATED APPLICATIONS

This Application is a U.S. National Stage Application under 35 U.S.C. §371 of PCT Application No. PCT/US2011/065730 filed Dec. 19, 2011 which claims priority under 35 U.S.C. §119(e) of U.S. Provisional Application No. 61/426,832 filed Dec. 23, 2010.

FIELD OF THE INVENTION

The present invention relates to certain quinolines and aza-quinolines of the Formula (I) (also referred to herein as the "compounds of the Formula (I)"), compositions comprising such compounds, and methods of using such compounds for treating an inflammatory disease, or other disorder mediated by the chemoattractant receptor-homologous molecule expressed on T-helper-type-2 cells (CRTH$_2$).

BACKGROUND OF THE INVENTION

Prostaglandin D$_2$ (PGD$_2$) belongs to a class of chemical mediators which cells synthesize in response to stimuli, such as local tissue damage or hormonal stimuli, or by cellular activation pathways. Cells synthesize PGD$_2$ from arachidonic acid by cyclooxygenase and other specific synthases in the pathway.

Upon stimulation, mast cells release PGD$_2$ in major amounts and this release plays a major role in the etiology of respiratory disease, such as asthma and congestion. PGD$_2$ achieves this effect by binding with either of two G-protein coupled receptors, which are the D-prostanoid (DP) receptor and the CRTH$_2$ receptor. TH-2 cells, eosinophils, and basophils express the CRTH$_2$ receptor, which mediates the chemoattractant effect of PGD$_2$.

Scientific studies support a clear role for PGD$_2$ in an allergic inflammatory response. PGD$_2$ is found at high levels in the bronchioalveolar lavage of asthmatics. Inhalation of PGD$_2$ enhances eosinophilic and lymphocytic airway inflammation in allergic animal models. Evidence obtained by studying CRTH$_2$ knockout mice demonstrates that PGD$_2$ achieves this enhancement by binding to the CRTH$_2$ receptor. Hence, CRTH$_2$ receptor antagonists would be expected to reduce the allergic inflammatory response caused by PGD$_2$, and these compounds would be useful in the treatment or prevention of allergic/immune disorders.

Current drugs of choice for the treatment of chronic inflammatory airway disease, such as asthma or COPD, are synthetic glucocorticoids; examples of these compounds currently indicated for treating these disorders include fluticasone and mometasone. The difficulty with treating patients with this class of compounds is that the compounds possess a number of systemic side-effects; these include adrenal suppression, altered bone metabolism and growth suppression in children. These side effects limit the dose that can be administered on a daily basis to the patient. While a non-steroidal class of therapeutics that inhibit bronchoconstriction exists (CysLT$_1$ antagonists), this class of compounds has limited efficacy in achieving the endpoints of reducing inflammatory and improving in lung function when compared to the glucocorticoids. Therefore, a therapeutic that combines the efficacy of inhaled glucocorticoids without the side effects would be advantageous.

SUMMARY OF THE INVENTION

In one aspect, the present invention provides a compound of the Formula (I):

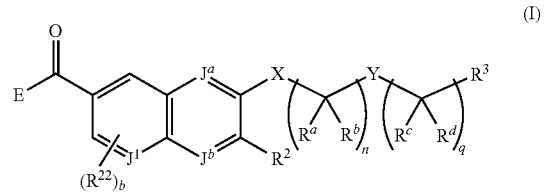

or a pharmaceutically acceptable salt thereof; wherein
one of J$^a$ and J$^b$ is N, and the other is C(H);
J$^1$ is C(H), C(R$^{22}$), or N;
E is selected from the group consisting of
(i) —N(R$^{6a}$)(R$^{6b}$), and
(ii) —O—C(R$^{7a}$)(R$^{7b}$)(R$^{7c}$),
R$^{6a}$ and R$^{6b}$ are independently:
a. H,
b. C$_1$-C$_{10}$ alkyl,
c. C$_3$-C$_6$ alkenyl,
d. C$_3$-C$_6$ alkynyl,
e. —O—(C$_1$-C$_3$ alkyl),
f. -Q-R$^{AH}$, wherein R$^{AH}$ is phenyl or 5- to 9-membered mono- or bicyclic heteroaryl containing 1 to 2 heteroatoms independently selected from the group consisting of N, O, and S,
and wherein R$^{AH}$ is unsubstituted or substituted with 1 to 5 moieties independently selected from the group consisting of halo, C$_1$-C$_3$ alkyl, C$_1$-C$_3$ alkoxy, C$_1$-C$_3$ fluoroalkyl, —O—(C$_1$-C$_3$ fluoroalkyl), hydroxyl, phenyl, and —CN;
Q is selected from the group consisting of a
(i) bond;
(ii) C$_1$-C$_6$ alkylene, wherein said C$_1$-C$_6$ alkylene is unsubstituted or substituted by 1 to 2 fluoro, C$_1$-C$_3$ alkyl, C$_1$-C$_3$ hydroxyalkyl, or C$_1$-C$_3$ fluoroalkyl; and
(iii)

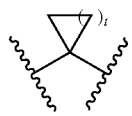

wherein t is 1, 2, 3, or 4;
g. -Q-R$^{HC}$, wherein R$^{HC}$ is
(i) 5- to 6-membered heterocyclyl containing 1 heteroatom selected from the group consisting of N and O, wherein said heterocyclyl of R$^{HC}$ is optionally fused to a benzene ring; or
(ii) C$_5$-C$_7$ cycloalkyl, wherein said cycloalkyl of R$^{HC}$ is optionally fused to a benzene ring;
and wherein R$^{HC}$ is unsubstituted or substituted with 1 to 5 R$^{12}$ moieties independently selected from the group consisting of halo, C$_1$-C$_3$ alkyl, C$_1$-C$_3$ alkoxy, C$_1$-C$_3$ fluoroalkyl, —O—(C$_1$-C$_3$ fluoroalkyl), hydroxyl, and —CN, or wherein when two R$^{12}$ moieties are geminally substituted on the same carbon atom, the two geminally substituted $R^{12}$ moieties, together with the carbon atom on which they are attached form —C(O)—;

h. or $R^{6a}$ and $R^{6b}$ together with the N atom to which they are attached form $R^{6H}$, wherein $R^{6H}$ is independently selected from the group consisting of:
  (i) a 4- to 7-membered heterocyclyl, optionally containing one additional nitrogen atom, wherein said heterocyclyl of $R^{6H}$ is optionally fused to phenyl; and
  (ii) a 4- to 7-membered heterocyclenyl, optionally containing one additional nitrogen atom, wherein said heterocyclenyl of $R^{6H}$ is optionally fused to phenyl;
  wherein $R^{6H}$ is unsubstituted or substituted by 1 to 5 $R^9$ moieties wherein each $R^9$ moiety is independently $C_1$-$C_6$ alkyl, $C_1$-$C_6$ alkoxy, fluoro, hydroxyl, —CN, —($C_1$-$C_3$ alkylene)-($C_1$-$C_3$ alkoxy), or
  $R^9$ is —Z—$R^{CY}$ wherein
  Z is
    (i) a bond,
    (ii) —C(O)—,
    (iv) —S(O)$_2$—, or
    (v) $C_1$-$C_3$ alkylene, wherein said $C_1$-$C_3$ alkylene of Z is optionally substituted by 1 to 2 fluoro or $C_1$-$C_3$ alkyl;
  $R^{CY}$ is selected from the group consisting of:
    (i) phenyl
    (ii) 5- to 10-membered mono or bicyclic heteroaryl containing 1 to 3 heteroatoms independently selected from the group consisting of N, O, and S; or
    (iii) 5- to 6-membered heterocyclyl containing 1 to 2 N atoms or 1 O atom, wherein said heterocyclyl of $R^{CY}$ is optionally fused to phenyl;
  wherein $R^{CY}$ is unsubstituted or substituted by 1 to 4 $R^{10}$ moieties;
  each $R^{10}$ moiety is independently $C_1$-$C_3$ alkyl, halo, hydroxyl, $C_1$-$C_3$ alkoxy, —($C_1$-$C_3$ alkylene)-($C_1$-$C_3$ alkoxy), —S(O)$_2$—($C_1$-$C_3$ alkyl), —C(O)—($C_1$-$C_3$ alkyl), —CN, or pyridyl, or, wherein when two $R^{10}$ moieties are geminally substituted on a common carbon atom, together with the carbon atom on which they are substituted, form —C(O)—;
  or, optionally, where two $R^9$ moieties are geminally substituted on a common ring carbon of $R^{6H}$, the two $R^9$ moieties, together with the ring carbon on which they are substituted, form $R^{YC}$, wherein $R^{YC}$ is
    (i) a 4- to 7-membered cycloalkyl, wherein said cycloalkyl of $R^{YC}$ is optionally fused to phenyl; or
    (ii) a 4- to 7-membered heterocyclyl containing 1 to 2 N atoms or 1 O atom, wherein said heterocyclyl of $R^{YC}$ is optionally fused to phenyl;
  wherein $R^{YC}$ is unsubstituted or substituted by 1 to 4 $R^{11}$ moieties;
  each $R^{11}$ moiety is independently $C_1$-$C_3$ alkyl, halo, hydroxyl, $C_1$-$C_3$ alkoxy, —($C_1$-$C_3$ alkylene)-($C_1$-$C_3$ alkoxy), —S(O)$_2$—($C_1$-$C_3$ alkyl), —C(O)—($C_1$-$C_3$ alkyl), phenyl, or pyridyl, or, wherein when two $R^{11}$ moieties are geminally substituted on a common carbon atom, together with the carbon atom on which they are substituted, form —C(O)—;

$R^{7a}$ and $R^{7b}$ are independently
  a) H,
  b) $C_1$-$C_6$ alkyl,
  c) phenyl wherein said phenyl is unsubstituted or substituted by 1 to 3 moieties independently selected from the group consisting of halo, $C_1$-$C_3$ alkyl, $C_1$-$C_3$ alkoxy, and CN; or
  d) $R^{7a}$ and $R^{7b}$ together with the carbon atom on which they are substituted, form $R^{PC}$, wherein $R^{PC}$ is
    (i) $C_3$-$C_7$ cycloalkyl, or
    (ii) phenyl, wherein said phenyl of $R^{PC}$ is unsubstituted or substituted by 1 to 5 moieties independently selected from the group consisting of halo, trifluoromethyl, and trifluoromethoxy;
$R^{7c}$ is
  a) H, or
  b) absent when $R^{7a}$ and $R^{7b}$ together with the carbon atom on which they are substituted form phenyl;
$R^{22}$ is halo, $C_1$-$C_3$ alkyl, or $C_1$-$C_3$ fluoroalkyl;
b is 0 or 1;
X is a bond, —O—, —S—, —S(O)—, or —S(O)$_2$—;
Y is selected from the group consisting of
  (i) a bond,

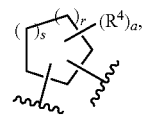
(ii)

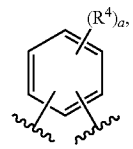
(iii)

(iv) —O—, (v) —S—, (v) —S(O)—, and (vii) —S(O)$_2$—;
wherein
  a is 0, 1, 2, or 3;
  r is 0, 1, or 2;
  s is 0, 1, or 2;
  each occurrence of $R^4$ is independently halo, $C_1$-$C_6$ alkyl, or $C_1$-$C_6$ fluoroalkyl;
$R^a$, $R^b$, $R^c$, and $R^d$ are independently H, fluoro, hydroxyl, $C_1$-$C_6$ alkyl, $C_1$-$C_6$ fluoroalkyl, or $C_1$-$C_6$ alkoxy;
$R^2$ is selected from the group consisting of:
  (i) phenyl;
  (ii) 5- to 6-membered heteroaryl containing from 1 to 3 heteroatoms selected from the group consisting of N, O, and S;
  (iii) 5- to 6-membered heterocyclenyl, containing from 1 to 2 heteroatoms selected from the group consisting of N, O, and S; and
  (iv) 5- to 6-membered heterocyclyl containing from 1 to 2 heteroatoms selected from the group consisting of N, O, and S;
  wherein $R^2$ is unsubstituted or substituted by 1 to 5 $R^5$ groups independently selected from the group consisting of halo, $C_1$-$C_3$ fluoroalkyl, $C_1$-$C_3$ alkyl, $C_1$-$C_3$ alkoxy, —CN, —OCF$_3$, —C(O)—($C_1$-$C_3$ alkyl), and —S(O)$_2$—($C_1$-$C_3$);

$R^3$ is —C(O)OH,

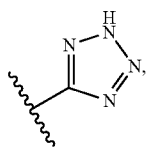 [SMILES: *c1nn[nH]n1]

or —N(H)—SO$_2$—R$^e$,
wherein R$^e$ is C$_1$-C$_6$ alkyl, C$_1$-C$_6$ fluoroalkyl, C$_1$-C$_6$ alkoxy, and phenyl;
n is 1, 2, 3, 4, or 5; and
q is 0, 1, or 2.

DETAILED DESCRIPTION OF THE INVENTION

Definitions

The terms used herein have their ordinary meaning and the meaning of such terms is independent at each occurrence thereof. That notwithstanding and except where stated otherwise, the following definitions apply throughout the specification and claims. Chemical names, common names, and chemical structures may be used interchangeably to describe the same structure. If a chemical compound is referred to using both a chemical structure and a chemical name, and an ambiguity exists between the structure and the name, the structure predominates. These definitions apply regardless of whether a term is used by itself or in combination with other terms, unless otherwise indicated. Hence, the definition of "alkyl" applies to "alkyl" as well as the "alkyl" portions of "hydroxyalkyl," "fluoroalkyl," "—O-alkyl," etc.

As used herein, and throughout this disclosure, the following terms, unless otherwise indicated, shall be understood to have the following meanings:

A "patient" is a human or non-human mammal. In one embodiment, a patient is a human. In another embodiment, a patient is a chimpanzee.

The term "therapeutically effective amount" as used herein, refers to an amount of the compound of Formula (I) and/or an additional therapeutic agent, or a composition thereof that is effective in producing the desired therapeutic, ameliorative, inhibitory or preventative effect when administered to a patient suffering from pain or an inflammatory disease or disorder. In the combination therapies of the present invention, a therapeutically effective amount can refer to each individual agent or to the combination as a whole, wherein the amounts of all agents administered are together effective, but wherein the component agent of the combination may not be present individually in an effective amount.

The term "preventing," as used herein with respect to pain or an inflammatory disease or disorder, refers to reducing the likelihood of pain or an inflammatory disease or disorder.

The term "alkyl," as used herein, refers to an aliphatic hydrocarbon group having one of its hydrogen atoms replaced with a bond. An alkyl group may be straight or branched and contain from about 1 to about 20 carbon atoms. In one embodiment, an alkyl group contains from about 1 to about 12 carbon atoms. In different embodiments, an alkyl group contains from 1 to 6 carbon atoms (C$_1$-C$_6$ alkyl) or from 1 to 3 carbon atoms (C$_1$-C$_3$ alkyl). Non-limiting examples of alkyl groups include methyl, ethyl, n-propyl, isopropyl, n-butyl, sec-butyl, isobutyl, tert-butyl, n-pentyl, neopentyl, isopentyl, n-hexyl, isohexyl and neohexyl. In one embodiment, an alkyl group is linear. In another embodiment, an alkyl group is branched. Unless otherwise indicated, an alkyl group is unsubstituted.

The term "alkylene," as used herein, refers to an alkyl group, as defined above, wherein one of the alkyl group's hydrogen atoms has been replaced with a bond. Non-limiting examples of alkylene groups include —CH$_2$—, —CH$_2$CH$_2$—, —CH$_2$CH$_2$CH$_2$—, —CH$_2$CH$_2$CH$_2$CH$_2$—, —CH(CH$_3$)CH$_2$CH$_2$—, —CH(CH$_3$)— and —CH$_2$CH(CH$_3$)CH$_2$—. In one embodiment, an alkylene group has from 1 to about 6 carbon atoms. In another embodiment, an alkylene group has from 1 to 3 carbon atoms. In another embodiment, an alkylene group is branched. In another embodiment, an alkylene group is linear. In one embodiment, an alkylene group is —CH$_2$—. The term "C$_1$-C$_3$ alkylene" refers to an alkylene group having from 1 to 3 carbon atoms. Unless otherwise indicated, an alkylene group is unsubstituted.

The term "alkenyl," as used herein, refers to an aliphatic hydrocarbon group containing at least one carbon-carbon double bond and having one of its hydrogen atoms replaced with a bond. An alkenyl group may be straight or branched and contain from about 2 to about 15 carbon atoms. In one embodiment, an alkenyl group contains from about 3 to 6 carbon atoms. Non-limiting examples of alkenyl groups include ethenyl, propenyl, n-butenyl, 3-methylbut-2-enyl, n-pentenyl, octenyl and decenyl. The term "C$_2$-C$_6$ alkenyl" refers to an alkenyl group having from 2 to 6 carbon atoms. Unless otherwise indicated, an alkenyl group is unsubstituted.

The term "alkenylene," as used herein, refers to an alkenyl group, as defined above, wherein one of the alkenyl group's hydrogen atoms has been replaced with a bond. Non-limiting examples of alkenylene groups include —CH$_2$CH=CH—, —CH$_2$CH=CHCH$_2$—, and —CH(CH$_3$)CH=CH—. In one embodiment, an alkenylene group has from 3 to 6 carbon atoms. In another embodiment, an alkenylene group is branched. In another embodiment, an alkenylene group is linear. The term "C$_3$-C$_6$ alkenylene" refers to an alkenylene group having from 3 to 6 carbon atoms. Unless otherwise indicated, an alkenylene group is unsubstituted.

The term "alkynyl," as used herein, refers to an aliphatic hydrocarbon group containing at least one carbon-carbon triple bond and having one of its hydrogen atoms replaced with a bond. An alkynyl group may be straight or branched and contain from about 2 to about 15 carbon atoms. In one embodiment, an alkynyl group contains from about 3 to about 6 carbon atoms. Non-limiting examples of alkynyl groups include ethynyl, propynyl, 2-butynyl and 3-methylbutynyl. Unless otherwise indicated, an alkynyl group is unsubstituted.

The term "alkynylene," as used herein, refers to an alkynyl group, as defined above, wherein one of the alkynyl group's hydrogen atoms has been replaced with a bond. Non-limiting examples of alkynylene groups include —CH$_2$C≡C—, —CH$_2$C≡CCH$_2$—, and —CH(CH$_3$)C≡C—. In one embodiment, an alkynylene group has from 3 to 6 carbon atoms. In another embodiment, an alkynylene group is branched. In another embodiment, an alkynylene group is linear. The term "C$_3$-C$_6$ alkynylene" refers to an alkynylene group having from 3 to 6 carbon atoms. Unless otherwise indicated, an alkenylene group is unsubstituted.

The term "alkoxy" as used herein, refers to an —O-alkyl group, wherein an alkyl group is as defined above. Non-limiting examples of alkoxy groups include methoxy, ethoxy, n-propoxy, isopropoxy, n-butoxy and t-butoxy. An alkoxy group is bonded via its oxygen atom.

The term "aryl," as used herein, refers to an aromatic monocyclic or multicyclic ring system comprising from about 6 to about 14 carbon atoms. In one embodiment, an aryl group contains from about 6 to 10 carbon atoms ($C_6$-$C_{10}$ aryl). In another embodiment an aryl group is phenyl. An aryl group can be optionally substituted with one or more "ring system substituents" which may be the same or different, and are as defined herein below. In one embodiment, an aryl group can be optionally fused to a cycloalkyl or cycloalkanoyl group. Non-limiting examples of aryl groups include phenyl and naphthyl. Unless otherwise indicated, an aryl group is unsubstituted.

The term "carbamyl," as used herein, refers to the moiety —C(O)NH$_2$ wherein the point of attachment is through the carbonyl carbon atom.

The term "cycloalkyl," as used herein, refers to a non-aromatic mono- or multicyclic ring system comprising from about 3 to about 10 ring carbon atoms. In one embodiment, a cycloalkyl contains from about 5 to 10 ring carbon atoms. In another embodiment, a cycloalkyl contains from about 3 to about 7 ring atoms. In another embodiment, a cycloalkyl contains from about 5 to about 6 ring atoms. Non-limiting examples of monocyclic cycloalkyls include cyclopropyl, cyclobutyl, cyclopentyl, cyclohexyl, cycloheptyl and cyclooctyl. Non-limiting examples of multicyclic cycloalkyls include 1-decalinyl, norbornyl and adamantyl. The term "$C_3$-$C_7$ cycloalkyl" refers to a cycloalkyl group having from 3 to 7 ring carbon atoms. Unless otherwise indicated, a cycloalkyl group is unsubstituted.

The term "halo," as used herein, means —F, —Cl, —Br or —I. In one embodiment, a halo group is —F or —Cl. In another embodiment, a halo group is —F.

The term "fluoroalkyl," as used herein, refers to an alkyl group as defined above, wherein one or more of the alkyl group's hydrogen atoms has been replaced with a fluorine. In one embodiment, a fluoroalkyl group has from 1 to 6 carbon atoms. In another embodiment, a fluoroalkyl group is substituted with from 1 to 3 F atoms. Non-limiting examples of fluoroalkyl groups include —CH$_2$F, —CHF$_2$, and —CF$_3$. The term "$C_1$-$C_3$ fluoroalkyl" refers to a fluoroalkyl group having from 1 to 3 carbon atoms.

The term "hydroxyalkyl," as used herein, refers to an alkyl group as defined above, wherein one of the alkyl group's hydrogen atoms has been replaced with a hydroxyl moiety. In one embodiment, a hydroxyalkyl group has from 1 to 3 carbon atoms. Non-limiting examples of hydroxyalkyl groups include —CH$_2$OH, —CH$_2$CH$_2$OH, and —CH$_2$CH(CH$_3$)CH$_2$OH, and —CH(CH$_3$)CH$_2$OH. The term "$C_1$-$C_3$ hydroxyalkyl" refers to a hydroxyalkyl group having from 1 to 3 carbon atoms.

The term "heteroaryl," as used herein, refers to an aromatic monocyclic or multicyclic ring system comprising about S to about 14 ring atoms, wherein from 1 to 4 of the ring atoms is independently O, N or S and the remaining ring atoms are carbon atoms. In one embodiment, a heteroaryl group has 5 to 10 ring atoms. In another embodiment, a heteroaryl group is monocyclic and has 5 or 6 ring atoms. In another embodiment, a heteroaryl group is bicyclic. A heteroaryl group is joined via a ring carbon atom, and any nitrogen atom of a heteroaryl can be optionally oxidized to the corresponding N-oxide. The term "heteroaryl" also encompasses a heteroaryl group, as defined above, which is fused to a benzene ring. Non-limiting examples of heteroaryls include pyridyl, pyrazinyl, furanyl, thienyl, pyrimidinyl, pyridone (including N-substituted pyridones), isoxazolyl, isothiazolyl, oxazolyl, oxadiazolyl, thiazolyl, pyrazolyl, furazanyl, pyrrolyl, triazolyl, 1,2,4-thiadiazolyl, pyrazinyl, pyridazinyl, quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, benzimidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like. In one embodiment, a heteroaryl group is a 5-membered heteroaryl. In another embodiment, a heteroaryl group is a 6-membered heteroaryl. In another embodiment, a heteroaryl group comprises a 5- to 6-membered heteroaryl group fused to a benzene ring. Unless otherwise indicated, a heteroaryl group is unsubstituted.

The term "heterocyclyl," as used herein, refers to a non-aromatic saturated monocyclic or multicyclic ring system comprising 3 to about 11 ring atoms, wherein from 1 to 4 of the ring atoms are independently O, S, or N, and the remainder of the ring atoms are carbon atoms. A heterocyclyl group can be joined via a ring carbon or ring nitrogen atom. In one embodiment, a heterocyclyl group is monocyclic and has from about 3 to about 7 ring atoms. In another embodiment, a heterocyclyl group is monocyclic has from about 4 to about 7 ring atoms. In another embodiment, a heterocyclyl group is bicyclic and has from about 7 to about 11 ring atoms. In still another embodiment, a heterocyclyl group is monocyclic and has 5 or 6 ring atoms. In one embodiment, a heterocyclyl group is monocyclic. In another embodiment, a heterocyclyl group is bicyclic. The term "heterocyclyl" also encompasses a heterocyclyl group, as defined above, which is fused to an aryl (e.g., benzene) or heteroaryl ring. The nitrogen or sulfur atom of the heterocyclyl can be optionally oxidized to the corresponding N-oxide, S-oxide or S,S-dioxide. Non-limiting examples of monocyclic heterocyclyl rings include oxetanyl, piperidyl, pyrrolidinyl, piperazinyl, morpholinyl, thiomorpholinyl, thiazolidinyl, 1,4-dioxanyl, tetrahydrofuranyl, tetrahydrothiophenyl, delta-lactam, delta-lactone, and the like.

In one embodiment, a heterocyclyl group is a 5- to 6-membered monocyclic heterocyclyl. In another embodiment, a heterocyclyl group is a 5-membered monocyclic heterocyclyl. In another embodiment, a heterocyclyl group is a 6-membered monocyclic heterocyclyl. The term "5- to 6-membered heterocyclyl" refers to a monocyclic heterocyclyl group having from 5 to 6 ring atoms. Unless otherwise indicated, a heterocyclyl group is unsubstituted.

"Heterocyclenyl" means a non-aromatic monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur atom, alone or in combination, and which contains at least one carbon-carbon double bond or carbon-nitrogen double bond. In specific embodiments of the ring system, from 1 to 4 of the ring atoms are independently O, S, or N, and the remainder of the ring atoms are carbon atoms. There are no adjacent oxygen and/or sulfur atoms present in the ring system. Preferred heterocyclenyl rings contain about 5 to about 6 ring atoms. The prefix aza, oxa or thia before the heterocyclenyl root name means that at least a nitrogen, oxygen or sulfur atom respectively is present as a ring atom. Unless otherwise indicated, a heterocyclenyl group is unsubstituted. The nitrogen or sulfur atom of the heterocyclenyl can be optionally oxidized to the corresponding N-oxide, S-oxide or S,S-dioxide. Non-limiting examples of suitable heterocyclenyl groups include 1,2,3,4-tetrahydropyridinyl, 1,2-dihydropyridinyl, 1,4-dihydropyridinyl, 1,2,3,6-tetrahydropyridinyl, 1,4,5,6-tetrahydropyrimidinyl, 2-pyrrolinyl, 3-pyrrolinyl, 2-imidazolinyl, 2-pyrazolinyl, dihydroimidazolyl, dihydrooxazolyl, dihydrooxadiazolyl, dihydrothiazolyl, 3,4-dihydro-2H-pyranyl, dihydrofuranyl, fluorodihydrofuranyl, 7-oxabicyclo[2.2.1]heptenyl, dihydrothiophenyl, dihydrothiopyranyl, and the like.

The term "substituted" means that one or more hydrogens on the atoms of the designated are replaced with a selection from the indicated group, provided that the atoms' normal valencies under the existing circumstances are not exceeded, and that the substitution results in a stable compound. Combinations of substituents and/or variables are permissible only if such combinations result in stable compounds. By "stable compound' or "stable structure" is meant a compound that is sufficiently robust to survive isolation to a useful degree of purity from a reaction mixture, and formulation into an efficacious therapeutic agent.

When any substituent or variable occurs more than one time in any constituent or the compound of Formula (I), its definition on each occurrence is independent of its definition at every other occurrence, unless otherwise indicated.

The term "in purified form," as used herein, refers to the physical state of a compound after the compound is isolated from a synthetic process (e.g., from a reaction mixture), a natural source, or a combination thereof. The term "in purified form," also refers to the physical state of a compound after the compound is obtained from a purification process or processes described herein or well-known to the skilled artisan (e.g., chromatography, recrystallization and the like), in sufficient purity to be characterizable by standard analytical techniques described herein or well-known to the skilled artisan.

It should also be noted that any carbon as well as heteroatom with unsatisfied valences in the text, schemes, examples and tables herein is assumed to have the sufficient number of hydrogen atom(s) to satisfy the valences.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

The compounds of Formula (I) may contain asymmetric or chiral centers, and, therefore, exist in different stereoisomeric forms. It is intended that all stereoisomeric forms of the compounds of Formula (I) as well as mixtures thereof, including racemic mixtures, form part of the present invention.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of Formula (I) may be atropisomers (e.g., substituted biaryls) and are considered as part of this invention. Enantiomers can also be separated by use of chiral HPLC column.

It is also possible that the compounds of Formula (I) may exist in different tautomeric forms, and all such forms are embraced within the scope of the invention.

All stereoisomers (for example, geometric isomers, optical isomers and the like) of the present compounds (including those of the salts and solvates of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention. Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the *IUPAC* 1974 Recommendations.

The compounds of Formula (I) can form salts which are also within the scope of this invention. Reference to a compound of Formula (I) herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of Formula (I) contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Such acidic and basic salts used within the scope of the invention are pharmaceutically acceptable (i.e., non-toxic, physiologically acceptable) salts. Salts of the compounds of Formula (I) may be formed, for example, by reacting a compound of Formula (I) with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates,) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use*. (2002) Zurich: Wiley-VCH; S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quarternized with agents such as lower alkyl halides (e.g., methyl, ethyl, and butyl chlorides, bromides and iodides), dialkyl sulfates (e.g., dimethyl, diethyl, and dibutyl sulfates), long chain halides (e.g., decyl, lauryl, and stearyl chlorides, bromides and iodides), aralkyl halides (e.g., benzyl and phenethyl bromides), and others.

The present invention further includes the compounds of Formula (I) in all their isolated forms. For example, the above-identified compounds are intended to encompass all forms of the compounds such as, any solvates, hydrates, stereoisomers, and tautomers thereof.

As used herein, the term "composition" is intended to encompass a product comprising the specified ingredients in the specified amounts, as well as any product which results, directly or indirectly, from combination of the specified ingredients in the specified amounts.

In the compounds of generic Formula (I), the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formula (I). For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within generic Formula (I) can be prepared without undue experimentation by conventional techniques well known to those skilled in the art or by processes analogous to those described in the Schemes and Examples herein using appropriate isotopically-enriched reagents and/or intermediates.

Compounds of the Invention

The present invention provides compound of Formula (I) or pharmaceutically acceptable salts thereof, wherein $J^1$, $J^a$, $J^b$, E, $R^2$, $R^3$, $R^{22}$, $R^a$, $R^b$, $R^c$, $R^d$, X, Y, b, n, and q are as defined above for the compound of Formula (I). The compounds of Formula (IA) and (IB), as are described in detail below, are embodiments of the compound of Formula (I).

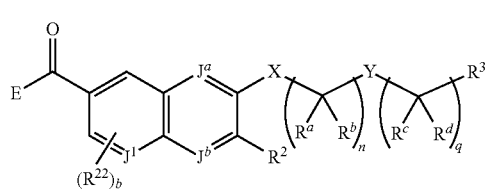

(I)

In specific embodiments of the compound of Formula (I), wherein E is —N($R^{6a}$)($R^{6b}$); and $R^{6a}$ and $R^{6b}$ together with the N atom to which they are attached form $R^{6H}$, it is be understood that two $R^9$ moieties can be geminally substituted on a common ring carbon of $R^{6H}$ to form $R^{YC}$, such that the group E-C(=O)— forms the group:

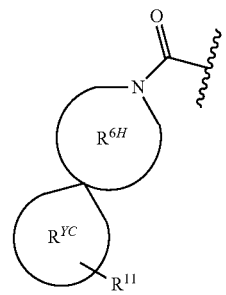

wherein $R^{6H}$ and $R^{YC}$ are as described above, and $R^{11}$ is either absent or present.

In certain embodiments of the compound of the Formula (I), wherein Y is

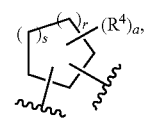

it is to be understood that the bonds joining the illustrated cycloalkyl ring to the chain can either be attached on different ring carbon atoms, e.g., on vicinal ring carbon atoms, or on the same ring carbon atom. For example, in some embodiments, the group

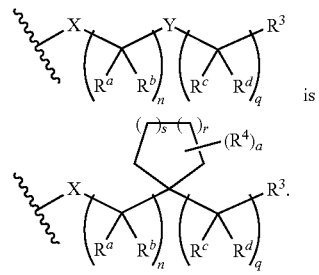

Described below are further embodiments of the compound of Formula (I).

In embodiment no. 1,
$J^1$ is C(H) or N;
E is selected from the group consisting of:
(i) —N($R^{6a}$)($R^{6b}$), and
(ii) —O—C(H)($R^{7a}$)($R^{7b}$),
  $R^{6a}$ and $R^{6b}$ are independently:
   a. H,
   b. $C_1$-$C_{10}$ alkyl,
   c. -Q-$R^{AH}$, wherein $R^{AH}$ is phenyl or 5- to 9-membered mono- or bicyclic heteroaryl containing 1 to 2 heteroatoms independently selected from the group consisting of N, O, and S,
   and wherein $R^{AH}$ is unsubstituted or substituted with 1 to 5 moieties independently selected from the group consisting of halo, $C_1$-$C_3$ alkyl, $C_1$-$C_3$ alkoxy, $C_1$-$C_3$ fluoroalkyl, —O—($C_1$-$C_3$ fluoroalkyl), hydroxyl, and —CN;
  Q is selected from the group consisting of:
   (a) a bond;
   (b) $C_1$-$C_6$ alkylene, wherein said $C_1$-$C_6$ alkylene is unsubstituted or substituted by 1 to 2 fluoro, $C_1$-$C_3$ alkyl, $C_1$-$C_3$ hydroxyalkyl, or $C_1$-$C_3$ fluoroalkyl; and (c)

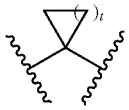

wherein t is 1, 2, 3, or 4;
d. -Q-R$^{HC}$, wherein R$^{HC}$ is
  (i) 5- to 6-membered heterocyclyl containing 1 heteroatom selected from the group consisting of N and O, wherein said heterocyclyl of R$^{HC}$ is optionally fused to a benzene ring; or
  (ii) C$_5$-C$_7$ cycloalkyl, wherein said cycloalkyl of R$^{HC}$ is optionally fused to a benzene ring;
  and wherein R$^{HC}$ is unsubstituted or substituted with 1 to 5 R$^{12}$ moieties independently selected from the group consisting of halo, C$_1$-C$_3$ alkyl, C$_1$-C$_3$ alkoxy, C$_1$-C$_3$ fluoroalkyl, —O—(C$_1$-C$_3$ fluoroalkyl), hydroxyl, and —CN, or wherein when two R$^{12}$ moieties are geminally substituted on the same carbon atom, the two geminally substituted R$^{12}$ moieties, together with the carbon atom on which they are attached form —C(O)—;
e. or R$^{6a}$ and R$^{6b}$ together with the N atom to which they are attached form R$^{6H}$, wherein R$^{6H}$ is independently selected from the group consisting of:
  (i) a 4- to 7-membered heterocyclyl, optionally containing one additional nitrogen atom, wherein said heterocyclyl of R$^{6H}$ is optionally fused to phenyl; and
  (ii) a 4- to 7-membered heterocyclenyl, optionally containing one additional nitrogen atom, wherein said heterocyclenyl of R$^{6H}$ is optionally fused to phenyl;
  wherein R$^{6H}$ is unsubstituted or substituted by 1 to 2 R$^9$ moieties wherein each R$^9$ moiety is independently C$_1$-C$_6$ alkyl, C$_1$-C$_6$ alkoxy, fluoro, hydroxyl, —CN, —(C$_1$-C$_3$ alkylene)-(C$_1$-C$_3$ alkoxy), or
  R$^9$ is —Z—R$^{CY}$ wherein
  Z is
  (i) a bond, or
  (ii) C$_1$-C$_3$ alkylene, wherein said C$_1$-C$_3$ alkylene of Z is optionally substituted by 1 to 2 fluoro or C$_1$-C$_3$ alkyl;
  R$^{CY}$ is selected from the group consisting of:
  (i) phenyl, or
  (ii) 5- to 10-membered mono or bicyclic heteroaryl containing 1 to 3 heteroatoms independently selected from the group consisting of N, O, and S;
  wherein R$^{CY}$ is unsubstituted or substituted by 1 to 2 R$^{10}$ moieties;
  each R$^{10}$ moiety is independently C$_1$-C$_3$ alkyl, halo, hydroxyl, C$_1$-C$_3$ alkoxy, —(C$_1$-C$_3$ alkylene)-(C$_1$-C$_3$ alkoxy), —S(O)$_2$—(C$_1$-C$_3$ alkyl), —C(O)—(C$_1$-C$_3$ alkyl), or —CN, or, wherein two R$^{10}$ moieties are geminally substituted on a common carbon atom, together with the carbon atom on which they are substituted, form —C(O)—;

R$^{7a}$ and R$^{7b}$ are independently
  a) H,
  b) C$_1$-C$_6$ alkyl, or
  c) phenyl wherein said phenyl is unsubstituted or substituted by 1 to 3 moieties independently selected from the group consisting of halo, C$_1$-C$_3$ alkyl, C$_1$-C$_3$ alkoxy, and CN;
b is 0;
X is a bond;
Y is a bond;
R$^a$, R$^b$, R$^c$, and R$^d$ are independently H or fluoro;
R$^2$ is selected from the group consisting of:
  (i) phenyl;
  (ii) 5- to 6-membered heteroaryl containing from 1 to 3 heteroatoms selected from the group consisting of N, O, and S;
  wherein R$^2$ is unsubstituted or substituted by 1 to 5 R$^5$ groups independently selected from the group consisting of halo, C$_1$-C$_3$ fluoroalkyl, C$_1$-C$_3$ alkyl, C$_1$-C$_3$ alkoxy, —CN, —OCF$_3$, —C(O)—(C$_1$-C$_3$ alkyl), and —S(O)$_2$—(C$_1$-C$_3$);
R$^3$ is —C(O)OH;
n is 1, 2, 3, 4, or 5; and
q is 0 or 1.

In embodiment no. 2, E is —N(R$^{6a}$)(R$^{6b}$), and the remaining variables are as described in the Summary of the Invention or in embodiment no. 1.

In embodiment no. 3, R$^1$ is —N(R$^{6a}$)(R$^{6b}$), and
  (i) R$^{6a}$ is H and
    R$^{6b}$ is -Q-R$^{AH}$ or -Q-R$^{HC}$; or
  (ii) R$^{6a}$ and R$^{6b}$ together with the N atom to which they are attached form R$^{6H}$; and the remaining radicals are as described in the Summary of the Invention or in embodiment no. 1.

In embodiment no. 4, E is —N(R$^{6a}$)(R$^{6b}$), wherein R$^{6a}$ is H, and R$^{6b}$ is -Q-R$^{AH}$ or -Q-R$^{HC}$. In specific instances of embodiment no. 4, R$^{6b}$ is -Q-R$^{HC}$, wherein Q is absent and R$^{HC}$ is

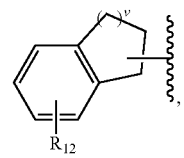

wherein v is 1 or 2, and R$^{12}$ is present or absent.

In embodiment no. 5, E is —N(R$^{6a}$)(R$^{6b}$) wherein R$^{6a}$ and R$^{6b}$ together with the N atom to which they are attached form R$^{6H}$. In specific instances of embodiment no. 5, R$^{6H}$ is

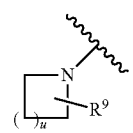

wherein u is 1, 2, or 3, and R$^9$ is present or absent.

In embodiment no. 6 of the compound of Formula (I), E is —O—C(R$^{7a}$)(R$^{7b}$)(R$^{7c}$), and the remaining radicals are as described in the Summary of the Invention or in embodiment no. 1. For example, in one instance of embodiment no. 6, E is —O—CH$_2$-Ph.

In embodiment no. 7, Y is selected from the group consisting of (i) a bond, (ii) 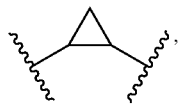

(iii) 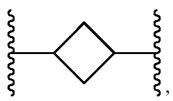

(iv) 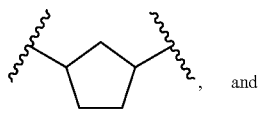, and (v) 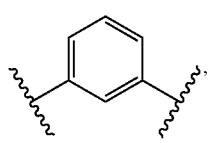

and the remaining variables of the compound of Formula (I) are as described in the Summary of the Invention or in any one of embodiment nos. 2-6.

In embodiment no. 8, the group

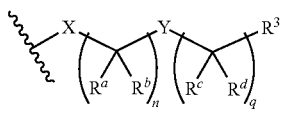

is selected from the group consisting of:

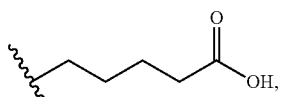

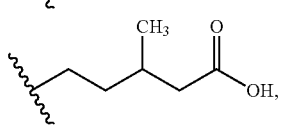

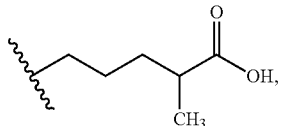

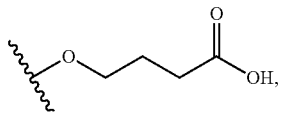

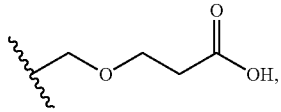

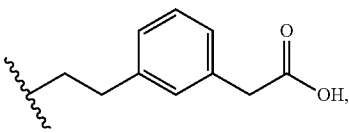

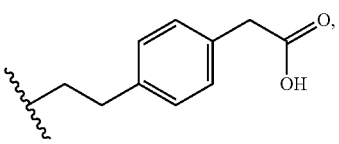

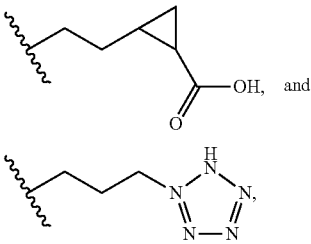

and the remaining radicals of the compound of Formula (I) are as described in the Summary of the Invention or in any one of embodiment nos. 2-6.

In embodiment no. 9, the group

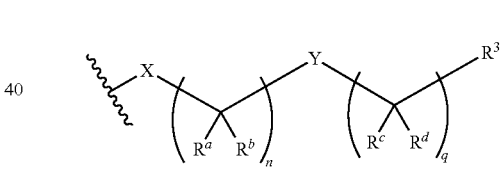

is

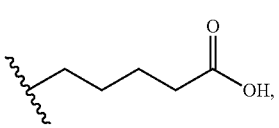 [SMILES: *CCCCC(=O)O]

and the remaining radicals of the compound of Formula (I) are as described in the Summary of the Invention or in any one of embodiment nos. 2-6.

In embodiment no. 10, $R^2$ is phenyl; wherein said phenyl is unsubstituted or substituted by 1 to 2 $R^5$ groups independently selected from the group consisting of fluoro, chloro, trifluoromethyl, $C_1$-$C_3$ alkoxy, —CN, and —$OCF_3$; and the remaining variables are as described in the Summary of the Invention or in any one of embodiment nos. 1-9.

In embodiment no. 11, b is 0, such that $R^{22}$ is absent; and the remaining variables are as described in the Summary of the Invention or in any one of embodiment nos. 1-9.

In embodiment no. 12, the compound of the Formula (I) has the Formula (IA)

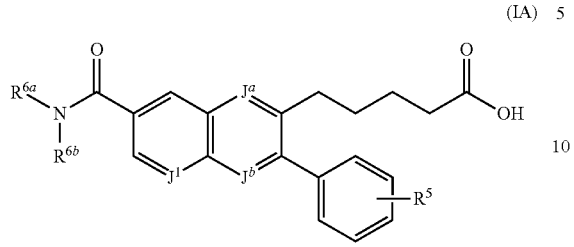
(IA)

wherein
J¹ is C(H) or N;
one of $J^a$ and $J^b$ is N, and the other is C(H);
$R^{6a}$ and $R^{6b}$ are independently:
a. H,
b. $C_1$-$C_{10}$ alkyl,
c. -Q-$R^{AH}$, wherein $R^{AH}$ is selected from the group consisting of:

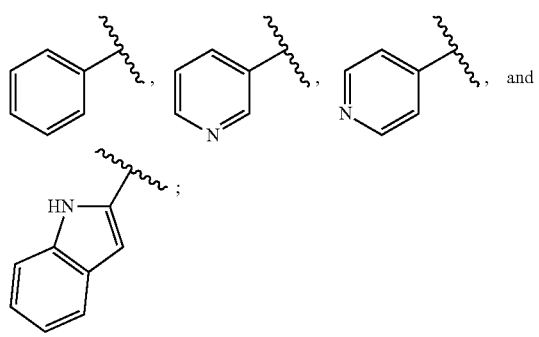

and wherein $R^{AH}$ is unsubstituted or substituted with 1 moiety selected from the group consisting of Cl, —CN, —CH₃, —CF₃, and —OCF₃;
Q is selected from the group consisting of a
(i) bond;
(ii) $C_1$-$C_3$ alkylene, wherein said alkylene is unsubstituted or substituted by one —CH₃, —CF₃, or —CH₂CH₂OH; and
d. -Q-$R^{HC}$, wherein $R^{HC}$ is selected from the group consisting of:

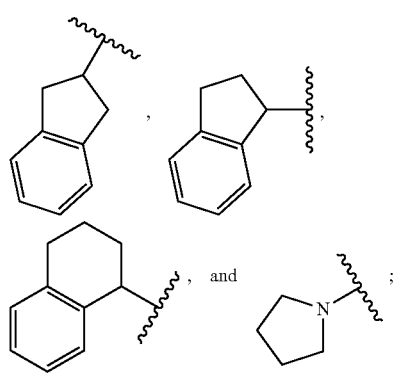

and wherein $R^{HC}$ is unsubstituted or substituted with 1 to 2 $R^{12}$ moieties independently selected from the group consisting of fluoro and chloro, or wherein when two $R^{12}$ moieties are geminally substituted on the same carbon atom, the two geminally substituted $R^{12}$ moieties, together with the carbon atom on which they are attached form —C(O)—;
e. or $R^{6a}$ and $R^{6b}$ together with the N atom to which they are attached form $R^{6H}$, wherein $R^{6H}$ is independently selected from the group consisting of:

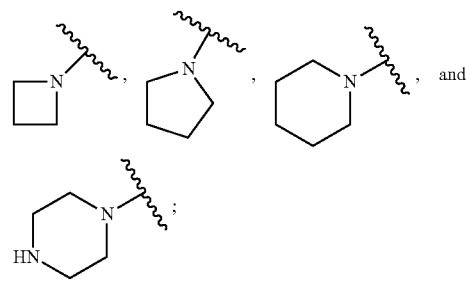

wherein $R^{6H}$ is unsubstituted or substituted by one $R^9$ moiety which is —Z—$R^{CY}$
wherein
Z is a bond; and
$R^{CY}$ is selected from the group consisting of:

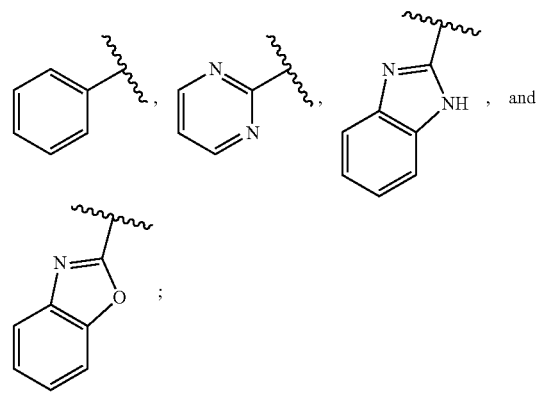

and
wherein $R^{CY}$ is unsubstituted or substituted by 1 to 2 $R^{10}$ moieties, wherein each $R^{10}$ moiety is independently selected from the group consisting of fluoro and chloro; and
$R^5$ is absent or present, and if present, is halo.

In embodiment no. 13, J¹ is C(H), and the structural formula and the remaining variables are as described above in embodiment no. 12.

In embodiment, no. 14, J¹ is C(H), $J^a$ is C(H) and $J^b$ is N, and the structural formula and the remaining variables are as described above in embodiment no. 12.

In embodiment, no. 15, J¹ is C(H), $J^a$ is N and $J^b$ is C(H), and the structural formula and the remaining variables are as described above in embodiment no. 12.

In embodiment, no. 16, J¹ is N, $J^a$ is C(H) and $J^b$ is N, and the structural formula and the remaining variables are as described above in embodiment no. 12.

In embodiment no. 17, the compound of the Formula (I) has the Formula (IB)

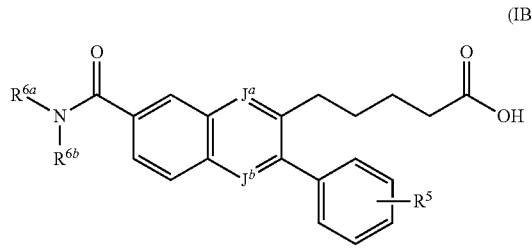

(IB)

wherein one of $J^a$ and $J^b$ is N and the other is C(H);
a) $R^{6a}$ is H and
  $R^{6b}$ is -Q-$R^{AH}$, wherein $R^{AH}$ is phenyl,
   wherein $R^{AH}$ is unsubstituted or substituted with moiety independently selected from the group consisting of fluoro, chloro, $C_1$-$C_3$ alkyl, and —O—($C_1$-$C_3$ fluoroalkyl);
  Q is methylene, wherein said methylene is unsubstituted or substituted by one $C_1$-$C_3$ alkyl or $C_1$-$C_3$ fluoroalkyl;
b) $R^{6a}$ is H and
  $R^{6b}$ is -Q-$R^{HC}$, wherein $R^{HC}$ is selected from the group consisting of:

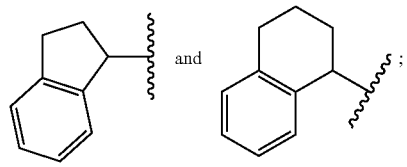 [SMILES: *C1CCc2ccccc21 ; *C1CCCc2ccccc21]

and wherein $R^{HC}$ is unsubstituted or substituted with 1 chloro;
c) or $R^{6a}$ and $R^{6b}$ together with the N atom to which they are attached form $R^{6H}$,
  wherein $R^{6H}$ is

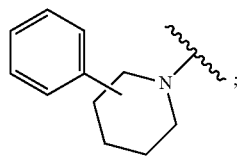

and
$R^5$ is absent or present, and if present, is fluoro.

In embodiment, no. 18, $J^a$ is C(H) and $J^b$ is N, and the structural formula and the remaining variables are as described above in embodiment no. 17.

In embodiment, no. 19, $J^a$ is N and $J^b$ is C(H), and the structural formula and the remaining variables are as described above in embodiment no. 17.

The invention also provides any one of the compounds specified in Tables A and B in the Examples section below, which tables include compounds 1, 1D, 1E, 1F, 1G, 1H, 1i, 1J, 1K, 1L, 1M, 1N, 1o, 1P, 1Q, 1R, 1S, 1T, 1U, 1V, 1W, 1Y, 1Z, 1AA, 1AB, 1AC, 1AD, 1AE, 1AF, 1AG, 1AH, 1Ai, 1AJ, 1AK, 1AL, 1AM, 1Ao, 1AP, 1AQ, 1AR, 1AS, 1AT, 1AU, 1AV, 1AW, 1AX, 1AY, 1AZ, 1BA, 1BB, 1BC, 1BD, 1BE, 2, 2A, 2B, 2C, 2D, 3, 3E, 3F, 3G, 3H, 3i, 3J, 3K, 3L, 4, 4E, 5, 5D, 5E, 5G, 5H, 5i, 5J, 5K, 5L, 5M, 5N, 5o, 5P, 5Q, 5R, 5S, 5T, 5U, 5V, 5W, 5X, 5Y, 5AA, 5AB, 5AC, 5AD, 5AE, 5AF, 5AG, 5AH, 5Ai, 5AJ, 5AK, 5AL, 5AM, 5AN, 5Ao, 5AP, 5AQ, 5AR, 5AS, 5AT, 5AU, 5AV, 5AW, 5AX, 5AY, 5AZ, 5BA, 5BB, 5BC, 5BD, 5BE, 5BF, 5BG, 5BH, 5Bi, 5BJ, 5BK, 5BL, 5BM, 5BN, 5Bo, 5BP, 5BQ, 5BR, 5BS, 5BT, 5BU, 6, 6D, 6E, 6F, 6G, 6H, 6i, 6J, 6K, 6L, 6M, 6N, 6o, 6P, 6Q, 6R, or a pharmaceutically acceptable salt thereof. The structures of these compounds are set forth in the Examples section below.

The invention also provides any one of the compounds specified in Table A in the Examples section below, which table includes compounds 1, 1D, 1E, 1F, 1G, 1H, 1i, 1J, 1K, 1L, 1M, 1N, 1o, 1P, 1Q, 1R, 1S, 1T, 1U, 1V, 1W, 1Y, 1Z, 1AA, 1AB, 1AC, 1AD, 1AE, 1AF, 1AG, 2, 2A, 2B, 2C, 2D, 3, 3E, 3F, 3G, 3H, 3i, 3J, 3K, 3L, 4, 4E, 5, 5D, 5E, 5G, 5H, 5i, 5J, 5K, 5L, 5M, 5N, 5o, 5P, 5Q, 5R, 5S, 5T, 5U, 5V, 5W, 5X, 5Y, 6, 6D, 6E, 6F, 6G, 6H, 6i, 6J, 6K, 6L, 6M, 6N, 6o, 6P, 6Q and 6R, or a pharmaceutically acceptable salt thereof.

In a specific embodiment, the invention also provides a compound selected from any one of compounds 1, 1D, 1E, 1L, 1T, 1AD, 1AE, 1AF, 1AG, 1M, 2, 2C, 3E, 4, 4E, 5G, 5o, and 6G, or a pharmaceutically acceptable salt thereof.

In another specific embodiment, the invention provides a compound selected from 1AH, 1Ai, 1AJ, 1AK, 1AL, 1AM, 1AN, 1Ao, 1AP, 1AQ, 1AR, 1AS, 1AT, 1AU, 1AV, 1AW, 1AX, 1AY, 1AZ, 1BA, 1BB, 1BC, 1BD, 1BE, 5AA, 5AB, 5AC, 5AD, 5AE, 5AF, 5AG, 5AH, 5Ai, 5AJ, 5AK, 5AL, 5AM, 5AN, 5Ao, 5AP, 5AQ, 5AR, 5AS, 5AT, 5AU, 5AV, 5AW, 5AX, 5AY, 5AZ, 5BA, 5BB, 5BC, 5BD, 5BE, 5BF, 5BG, 5BH, 5Bi, 5BJ, 5BK, 5BL, 5BM, 5BN, 5Bo, 5BP, 5BQ, 5BR, 5BS, 5BT, and 5BU, or a pharmaceutically acceptable salt thereof.

The invention also provides a compound of Formula (I) or a pharmaceutically acceptable salt thereof in purified form.

Compositions and Administration

This invention is also directed to pharmaceutical compositions which comprise a compound of Formula (I), or a pharmaceutically acceptable salt of said compound and a pharmaceutically acceptable carrier.

A preferred dosage is about 0.001 to 100 mg/kg of body weight/day of the compound of Formula (I). An especially preferred dosage is about 0.01 to 10 mg/kg of body weight/day of a compound of Formula (I), or a pharmaceutically acceptable salt of said compound.

The term "pharmaceutical composition" is also intended to encompass both the bulk composition and individual dosage units comprised of more than one (e.g., two) pharmaceutically active agents such as, for example, a compound of the present invention and an additional therapeutic agent selected from the lists of the additional agents described herein below, along with any pharmaceutically inactive excipients. The bulk composition and each individual dosage unit can contain fixed amounts of the aforesaid "more than one pharmaceutically active agents". The bulk composition is material that has not yet been formed into individual dosage units. An illustrative dosage unit is an oral dosage unit such as tablets, pills and the like. Similarly, the herein-described method of treating a patient by administering a pharmaceutical composition of the present invention is also intended to encompass the administration of the afore-said bulk composition and individual dosage units.

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g., magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), *Remington's Pharmaceutical Sciences*, 18$^{th}$ Edition, (1990), Mack Publishing Co., Easton, Pa.

Liquid form preparations include solutions, suspensions and emulsions. Examples of materials useful for forming such liquid form preparations include water or water-propylene glycol solutions for parenteral injection, or sweeteners and opacifiers for oral solutions, suspensions and emulsions. Liquid form preparations may also include solutions or suspensions for intranasal administration.

Aerosol preparations suitable for inhalation may include solutions and solids in powder form, which may be in combination with a pharmaceutically acceptable carrier, such as an inert compressed gas, e.g., nitrogen.

Also included are solid form preparations that are intended to be converted, shortly before use, to liquid form preparations for either oral or parenteral administration. Such liquid forms include solutions, suspensions and emulsions.

The compounds of the invention can also be deliverable transdermally. The transdermal compositions can take the form of creams, lotions, aerosols and/or emulsions and can be included in a transdermal patch of the matrix or reservoir type as are conventional in the art for this purpose.

The compounds of this invention may also be delivered subcutaneously.

Preferably the compound is administered orally.

Preferably, the pharmaceutical preparation is in a unit dosage form. In such form, the preparation is subdivided into suitably sized unit doses containing appropriate quantities of the active component, e.g., an effective amount to achieve the desired purpose.

The quantity of active compound in a unit dose of preparation may be varied or adjusted from about 0.001 mg to about 100 mg per kg body weight of a mammal, preferably from about 0.01 mg to about 10 mg per kg. The actual dosage employed may be varied depending upon the requirements of the patient and the severity of the condition being treated. Determination of the proper dosage regimen for a particular situation is within the skill of the art. For convenience, the total daily dosage may be divided and administered in portions during the day as required.

The compositions of the invention can further comprise one or more additional therapeutic agents, as discussed in further detail below. Accordingly, in one embodiment, the present invention provides compositions comprising: (i) a compound of Formula (I) or a pharmaceutically acceptable salt thereof; (ii) one or more additional therapeutic agents, that are not compounds of Formula (I); and (iii) a pharmaceutically acceptable carrier, wherein the amounts in the composition are together effective to treat one of the disease or conditions discussed above.

Uses of the Compounds

The compounds of Formula (I) bind to CRTH$_2$ and, therefore, are useful in characterizing tissues containing CRTH$_2$, and in identifying further compounds which bind to CRTH$_2$.

The general value of the compounds of the invention in binding the CRTH$_2$ receptor can be determined, for example, using the radioligand binding assay described below in the Examples section.

The compounds of Formula (I) can also be useful as modulators of CRTH$_2$ receptor function. In some embodiments, compounds of Formula (I) are antagonists of the CRTH$_2$ receptor. The general value of the compounds of the invention in antagonizing CRTH$_2$ receptor function can be determined, for example, using the chemiluminescent-based cAMP assay, the β-Arrestin assay, or the eosinophil shape change assay described below in the Examples section.

While not being bound by any specific theory, Applicants believe that the compounds of Formula (I) are useful in treating the symptoms of diseases or conditions associated with uncontrolled or inappropriate stimulation of CRTH$_2$ function because of their ability to antagonize the CRTH$_2$ receptor. Accordingly, in one embodiment, the invention provides a method for treating a disease or conditions associated with uncontrolled or inappropriate stimulation of CRTH2 function, comprising administering a therapeutically effective amount of a compound of Formula (I) to a patient in need of such treatment. In certain embodiments, the compound of Formula (I) used in the method is selected from one of the representative compounds listed in Table A and B as set forth in the Examples section.

Diseases or conditions associated with uncontrolled or inappropriate stimulation of CRTH$_2$ function include (but not limited to) asthma, congestion, allergic rhinitis, atopic dermatitis, chronic obstructive pulmonary disease ("COPD"), dermatitis, inflammatory bowel disease, rheumatoid arthritis, allergic nephritis, conjunctivitis, bronchial asthma, fold allergy, systemic mast cell disorder, anaphylactic shock, urticaria, eczema, itching, inflammation, ischemia-reperfusion injury, cerebrovascular disorders, pleuritis, ulcerative colitis, eosinophil-related diseases, such as Churg-Strauss syndrome and sinusitis, and basophile-related diseases, such as basophilic leukemia and basophilic leukocytosis, in humans and other mammals. Examples of cerebrovascular disorders include stroke.

In certain embodiments, the present invention provides a method for treating asthma, congestion, allergic rhinitis or COPD which comprises administering a therapeutically effective dose of a compound of Formula (I) or a pharmaceutically acceptable salt thereof to a patient in need of such treatment. In a specific embodiment, the disease or condition being treated is asthma. In another embodiment, the disease or condition being treated is COPD.

In addition, compounds of the Formula (I) which act as CRTH$_2$ receptor antagonists can inhibit prostanoid-induced smooth muscle contraction by antagonizing contractile prostanoids or mimicking relaxing prostanoids and hence may be used in the treatment of dysmenorrhea, premature labor and eosinophil related disorders.

In another embodiment, the present invention provides a compound of Formula (I) or a pharmaceutically acceptable salt thereof for use in the manufacture of a medicament for treating a disease or condition selected from the group consisting of asthma, congestion, allergic rhinitis, atopic dermatitis, COPD, dermatitis, inflammatory bowel disease, rheumatoid arthritis, allergic nephritis, conjunctivitis, bronchial asthma, food allergy, systemic mast cell disorder, anaphylactic shock, urticaria, eczema, itching, inflammation, ischemia-reperfusion injury, cerebrovascular disorders, pleuritis, ulcerative colitis, eosinophil-related diseases, such as Churg-Strauss syndrome and sinusitis, and basophile-related diseases, such as basophilic leukemia and basophilic leukocytosis. In certain embodiments of the use, the compound of Formula (I) is selected from one of the representative compounds listed in Table A and B as set forth in the Examples section.

In another embodiment, the present invention provides a compound of Formula (I) or a pharmaceutically acceptable salt thereof for use in treating a disease or condition from the group consisting of asthma, congestion, allergic rhinitis, atopic dermatitis, COPD, dermatitis, inflammatory bowel disease, rheumatoid arthritis, allergic nephritis, conjunctivitis, bronchial asthma, food allergy, systemic mast cell disorder, anaphylactic shock, urticaria, eczema, itching, inflammation, ischemia-reperfusion injury, cerebrovascular disorders, pleuritis, ulcerative colitis, eosinophil-related diseases, such as Churg-Strauss syndrome and sinusitis, and basophile-related diseases, such as basophilic leukemia and basophilic leukocytosis. In certain embodiments of the use, the compound of Formula (I) is selected from one of the representative compounds listed in Table A and B as set forth in the Examples section.

In specific embodiments of the methods and uses described above, the compound used in the method or use described above is selected one of the compounds 1, 1D, 1E, 1F, 1G, 1H, 1i, 1J, 1K, 1L, 1N, 1o, 1P, 1Q, 1R, 1S, 1T, 1U, 1V, 1W, 1X, 1Y, 1Z, 1AA, 1AB, 1AC, 1AD, 1AE, 1AF, 1AG, 2, 2A, 2B, 2C, 2D, 3, 3E, 3F, 3, 3i, 3J, 4, 4E, 5, 5D, 5E, 5F, 5G, 5H, 5i, 5J, 5K, 5L, 5M, 5N, 5o, 5P, 5Q, 5R, 5S, 5T, 5U, 5V, 5W, 5X, 5Y, 6, 6D, 6F, 6G, 6H, 6i, 6J, 6K, 6L, 6M, 6N, 6o, 6P, 6Q, and 6R or a pharmaceutically acceptable salt thereof.

Combination Therapy

The compounds of Formula (I) or their pharmaceutically acceptable salts may be used in combination, either in a single formulation or co-administered as separate formulations with at least one additional therapeutic agent to treat or prevent the diseases and conditions described herein. These additional therapeutic agents include, but are not limited to: (1) a DP receptor antagonist, such as S-5751 and laropiprant; (2) a corticosteroid, such as triamcinolone acetonide, budesonide, beclomethasone, fluticasone and mometasone; (3) a β2-adrenergic agonist, such as salmeterol, formoterol, aformoterol, terbutaline, metaproterenol, albuterol and the like; (4) a leukotriene modifier, including a leukotriene receptor antagonist, such as montelukast, zafirlukast, pranlukast, or a lipooxygenase inhibitor including 5-lipooxygenase inhibitors and FLAP (5-lipooxygenase activating protein) inhibitors, such as zileuton; (5) an antihistamine such as bromopheniramine, chlorpheniramine, dexchlorpheniramine, triprolidine, clemastine, diphenhydramine, diphenylpyraline, tripelennamine, hydroxyzine, methdilazine, promethazine, trimeprazine, azatadine, cyproheptadine, antazoline, pheniramine pyrilamine, astemizole, terfenadine, loratadine, cetirizine, fexofenadine, descarboethoxyloratadine, and the like; (6) a decongestant, including phenylephrine, phenylpropanolamine, pseudophedrine, oxymetazoline, ephinephrine, naphazoline, xylometazoline, propylhexedrine, or levo-desoxyephedrine; (7) an antiitussive, including codeine, hydrocodone, caramiphen, carbetapentane, or dextramethorphan; (8) another prostaglandin ligand, including prostaglandin F agonist such as latanoprost; misoprostol, enprostil, rioprostil, ornoprostol or rosaprostol; (9) a diuretic; (10) non-steroidal antiinflammatory agents (NSAIDs), such as propionic acid derivatives (alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid, and tioxaprofen), acetic acid derivatives (indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin, and zomepirac), fenamic acid derivatives (flufenamic acid, meclofenamic acid, mefenamic acid, niflumic acid and tolfenamic acid), biphenylcarboxylic acid derivatives (diflunisal and flufenisal), oxicams (isoxicam, piroxicam, sudoxicam and tenoxican), salicylates (acetyl salicylic acid, sulfasalazine) and the pyrazolones (apazone, bezpiperylon, feprazone, mofebutazone, oxyphenbutazone, phenylbutazone); (11) cyclooxygenase-2 (COX-2) inhibitors, such as celecoxib and rofecoxib; (12) inhibitors of phosphodiesterase type IV (PDE-IV) e.g., Ariflo, roflumilast; (13) antagonists of the chemokine receptors, especially CCR-1, CCR-2, and CCR-3; (14) cholesterol lowering agents such as HMG-CoA reductase inhibitors (lovastatin, simvastatin and pravastatin, fluvastatin, atorvastatin, and other statins), sequestrants (cholestyramine and colestipol), nicotinic acid, fenofibric acid derivatives (gemfibrozil, clofibrat, fenofibrate and benzafibrate), and probucol; (15) anti-diabetic agents such as insulin, sulfonylureas, biguanides (metformin), α-glucosidase inhibitors (acarbose) and glitazones (troglitazone, pioglitazone, englitazone, rosiglitazone and the like); (16) preparations of interferon beta (interferon beta-1a, interferon beta-1b); (17) anticholinergic agents, such as muscarinic antagonists (ipratropium bromide and tiotropium bromide), as well as selective muscarinic M3 antagonists; (18) steroids such as beclomethasone, methylprednisolone, betamethasone, prednisone, dexamethasone, and hydrocortisone; (19) triptans commonly used for the treatment of migraine such as sumitriptan and rizatriptan; (20) alendronate and other treatments for osteoporosis; (21) other compounds such as 5-aminosalicylic acid and prodrugs thereof, antimetabolites such as azathioprine and 6-mercaptopurine, cytotoxic cancer chemotherapeutic agents, bradykinin (BK2) antagonists such as FK-3657, TP receptor antagonists such as seratrodast, neurokinin antagonists (NK1/NK2), VLA-4 antagonists, such as those described in U.S. Pat. No. 5,510,332, WO97/03094, WO97/02289, WO96/40781, WO96/22966, WO96/20216, WO96/01644, WO96/06108, WO95/15973 and WO96/31206. In addition, the invention encompasses a method of treating prostaglandin D2 mediated diseases comprising: administration to a patient in need of such treatment a non-toxic therapeutically effective amount of a compound of Formula (I), optionally co-administered with one or more of such ingredients as listed immediately above.

When administering a combination therapy to a patient in need of such administration, the therapeutic agents in the combination, or a pharmaceutical composition or compositions comprising the therapeutic agents, may be administered in any order such as, for example, sequentially, concurrently, together, simultaneously and the like.

In one embodiment, the compound of Formula (I) is administered during a time when the additional therapeutic agent(s) exert their prophylactic or therapeutic effect, or vice versa.

In another embodiment, the compound of Formula (I) and the additional therapeutic agent(s) are administered in doses commonly employed when such agents are used as monotherapy for treating the disorder.

In another embodiment, the compound of Formula (I) and the additional therapeutic agent(s) are administered in doses lower than the doses commonly employed when such agents are used as monotherapy for treating the disorder.

In one embodiment, the compound of Formula (I) and the additional therapeutic agent(s) are present in the same composition, which is suitable for oral administration.

The compound of Formula (I) and the additional therapeutic agent(s) can act additively or synergistically. A synergistic combination may allow the use of lower dosages of one or more agents and/or less frequent administration of one or more agents of a combination therapy. A lower dosage or less frequent administration of one or more agents may lower toxicity of the therapy without reducing the efficacy of the therapy.

The doses and dosage regimen of the additional therapeutic agent(s) used in the combination therapies of the present invention for the treatment or prevention of a disease or disorder can be determined by the attending clinician, taking into consideration the approved doses and dosage regimen in the package insert; the age, sex and general health of the patient; and the type and severity of the viral infection or related disease or disorder.

Another aspect of this invention is a kit comprising a therapeutically effective amount of the compound of Formula (I) or a pharmaceutically acceptable salt of said compound, optionally at least one additional therapeutic agent listed above and a pharmaceutically acceptable carrier, vehicle or diluent.

Methods of Preparing the Compounds of Formula (I)

In general, the compounds in the invention may be produced by a variety of processes known to those skilled in the art and by know, processes analogous thereto. The invention disclosed herein is exemplified by the following preparations and examples which should not be construed to limit the scope of the disclosure. Alternative mechanistic pathways and analogous structures will be apparent to those skilled in the art. The practitioner is not limited to these methods.

One skilled in the art will recognize that one route will be optimized depending on the choice of appendage substituents. Additionally, one skilled in the art will recognize that in some cases the order of steps has to be controlled to avoid functional group incompatability.

The prepared compounds may be analyzed for their composition and purity as well as characterized by standard analytical techniques such as, for example, elemental analysis, NMR, mass spectroscopy and IR spectra.

One skilled in the art will recognize that reagents and solvents actually used may be selected from several reagents and solvents well known in the art to be effective equivalents. Hence, when a specific solvent or reagent is mentioned, it is meant to be an illustrative example of the conditions desirable for that particular reaction scheme or for the preparation described below.

Where NMR data are presented, $^1$H spectra were obtained on either a Varian VXR-400 (400 MHz, 1H), Varian Gemini-300 (300 MHz), Varian Mercury VX-400 (400 MHz), Bruker-Biospin AV-500 (500 MHz) or Bruker Avance DRX-500 (500 MHz), and chemical shifts are reported as ppm with number of protons and multiplicities indicated parenthetically. Where LC/MS data are presented, analyses was performed using a 1200 series Agilent 6140 Quadrupole LCMS with a 1.8 μM Zorbax SB-C18 column (10-95% of MeCN—H$_2$O with 0.1% TFA over 2.7 min, 1 mL/min) or with an Applied Biosystems API-150 mass spectrometer and Gemini C18 column (50×4.6 mm, 10-95% CH$_3$CN—H$_2$O with 0.05% TFA over 5 min, 1 mL/min).

The following solvents, reagents, protecting groups, moieties, and other designations may be referred to by their abbreviations in parenthesis:

Me=methyl; Et=ethyl; Pr=propyl; Bu=butyl; t-Bu=tert-butyl; Ph=phenyl, and Ac=acetyl
μ=microliters
Acac=acetylacetone
AcOEt or EtOAc=ethyl acetate
AcOH or HOAc=acetic acid
ACN=acetonitrile
aq=aqueous
Ar=aryl
atm=atmosphere
9-BBN=9-borabicyclo[3.3.1]nonane
Bn=benzyl
Boc or BOC=tert-butoxycarbonyl
Bz=benzoyl
Boc=tert-butoxycarbonyl
BINAP=2,2'-bis(diphenylphosphino)-1,1'-bisnaphthyl
cat=catalyst or catalytic
Cbz=benzyloxycarbonyl
DBU=1,8-Diaza-7-bicyclo[5.4.0]undecene
dcpp-2(HBF)4=1,3-bis(dicyclohexyl)phosphonium)propane bis(tetrafluoroborate)
DCM or CH2Cl2: dichloromethane:
DMAP=4-Dimethylaminopyridine
DIBAL=diisobutylaluminum hydride
DIPEA or Hünig's Base=N,N-diisopropylethylamine
DME=1,2-dimethoxyethane
DMF=dimethylformamide
DMS=dimethylsulfide
DMSO=dimethyl sulfoxide
Dppf=1,1'-bis(diphenylphosphino)ferrocene
EDCI or DEC=1-(3-dimethylaminopropyl)-3-ethylcarbodiimide
g=grams
h=hour
HetAr=heteroaryl
HMDS=1,1,1,3,3,3-hexamethyldisilazane
HATU=N,N,N',N'-tetramethyl-O-(7-azabenzotriazol-1-yl)uranium hexafluorophosphate
HOBt=1-hydroxybenzotriazole
Im=imidazole
LAN=lithium aluminum hydride
LDA=lithium diisopropylamide
LCMS=liquid chromatography mass spectrometry
LG=leaving group
min=minute
mg=milligrams
mL=milliliters
mmol=millimoles
MeOH: methanol
MS=mass spectrometry
NBS=N-bromosuccimide
NMR=nuclear magnetic resonance spectroscopy
PG=protecting group
Pyr=pyridine
rac or (±)=racemic mixture or enantiomers
RT or rt=room temperature (ambient, about 25° C.)
sat=saturated
SM=starting material
TBSCI=t-butyldimethylsilyl chloride
TBS=t-butyldimethyl silyl
TEA=triethylamine (Et$_3$N)
TFA=trifluoroacetic acid
TFAA=trifluoroacetic anhydride
THF=tetrahydrofuran TLC=thin layer chromatography
TMS=trimethylsilyl
Tos or Ts=p-toluenesulfonyl (tosyl)
Tol=toluene
IBMX=3-Isobutyl-1-methylxanthine
HBSS=Hank's balanced salt solution
HEPES=1-[4-(2-Hydroxyethyl)-1-piperazinyl]ethane-2-sulfonic acid The compounds of this invention can be prepared through the general approach outlined in the following schemes. These schemes are being provided to illustrate the present invention. To assist one in this endeavor, the ordinary practitioner would have full knowledge of literature sources such as *Chemical Abstracts; Beilstein, Protective Groups in Organic Synthesis* 2$^{nd}$ *Edition* T. W. Greene, P. G. M. Wuts 1991, Wiley and Sons; *Comprehensive Organic Transformations, Advanced Organic Chemistry* etc.

Scheme 1 shows an approach in which a substituted aminobenzaldehyde S1 is subjected to a Friedlander quinoline synthesis with ketone S3 (in which $R^2$ is aryl or heteroaryl and $Y^S$ is a linker) and hydroxide base to provide S2.

Left side transformation, in which A is a functional group such as an ester, nitrile, halogen, optionally functionalized alcohol, or other group, to A=one of the various definitions of $R^1$, such as amide) occurs by a process known to a practitioner in then art. For example, an activated alcohol or halogen may be carbonylated by a metal catalyzed or metal-facilitated process to provide an ester or acid, which may be further transformed to an amide or ketone. When converting an acid to an amide, an appropriate amine and coupling agent (as EDCI, HOBt, PyBop, HATU etc.) or activation method (oxalyl chloride, thionyl chloride etc.) may be used.

SCHEME 1

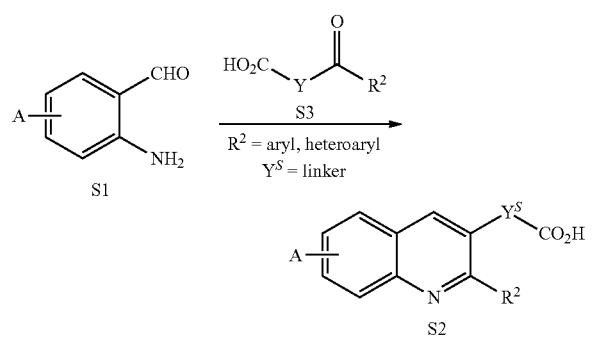

Scheme 2 shows an approach in which a substituted aminobenzaldehyde S1 is treated with the ketone S5 (in which $R^2$ is aryl or heteroaryl and $Y^S$ is an alkyl linker) and hydroxide base to provide S4.

SCHEME 2

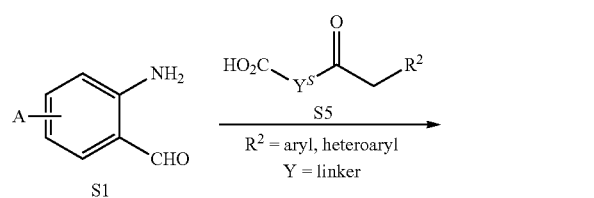

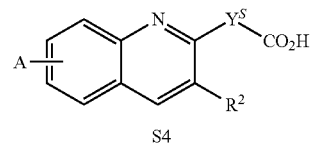

Scheme 3 shows an approach in which a substituted aminobenzaldehyde S1 is treated with the substituted acetic acid S8 (in which $R^2$ is aryl or heteroaryl; activated with acetic anhydride or the like) to provide S6a (R'=OH). This intermediate is then converted to S6b (wherein R'=OTf, Cl, Br or other suitable group by treatment with $POCl_3$, $SOCl_2$, $P_2O_5$/$Bu_4NCl$, $P_2O_5$/$Bu_4NBr$, $Tf_2O$, $PhNTf_2$ etc.), coupled with S9 (which has been preactivated via a hydroboration reaction with 9-BBN or similar boron-based reagent; $Y^S$=a suitable alkyl, cycloalkyl, aryl or heterocylic linker; $R^{3S}$=ester or other appropriate group, such a as nitrile or alcohol) to provide S7a. Final conversion to S7b is then achieved by one of many appropriate synthetic methods known to practitioners in the art (such as acid- or base-hydrolysis when $R^{3S}$=ester, oxidation when $R^{3S}$=alcohol, hydrolysis when $R^{3S}$=nitrile etc).

SCHEME 3

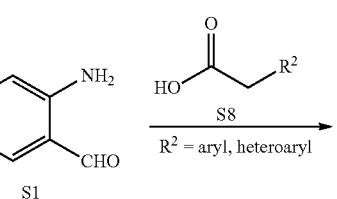

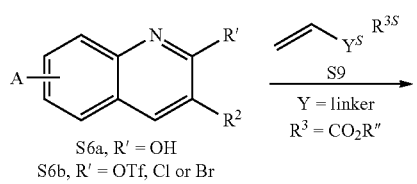

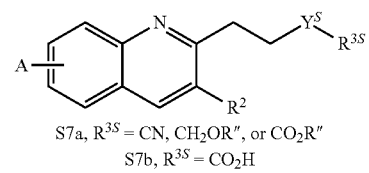

The starting materials (such as S1, S3, S5, S8, and S9) and reagents used in preparing compounds described are either available from commercial suppliers such as Aldrich Chemical Co. (Wisconsin, USA) and Acros Organics Co. (New Jersey, USA) or were prepared by literature methods known to those skilled in the art.

Compounds, such as those described by formulae S5, S4, and S7b can be prepared by the general methods outlined above. Exemplary compounds were prepared as described in the examples below or from starting materials known in the art. When unavailable from commercial suppliers, starting materials are synthesized according to methods known in the literature. These examples are being provided to further illustrate the present invention. They are for illustrative purposes only; the scope of the invention is not to be considered limited in any way thereby.

EXAMPLES

Example 1

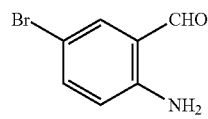

Step 1

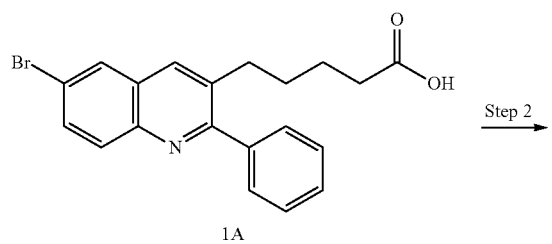

1A

Step 2

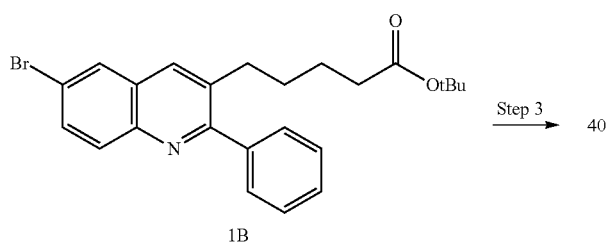

1B

Step 3

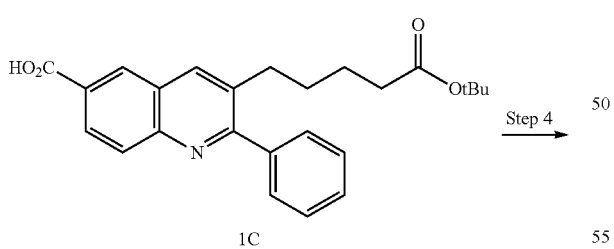

1C

Step 4

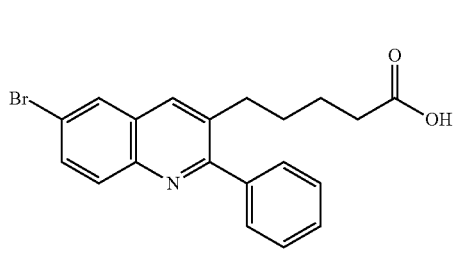

1

Step 1

5-(6-bromo-2-phenylquinolin-3-yl)pentanoic acid

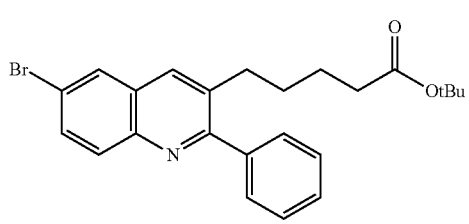

1A

7-Oxo-7-phenylheptanoic acid (5.00 g, 22.7 mmol) and 2-amino-5-bromobenzaldehyde (5.45 g, 27.2 mmol) were dissolved in a solution of methanol (100 mL) and 2 M NaOH (30 mL). The reaction mixture was heated to 110° C. in an oil bath and refluxed overnight. The reaction was concentrated, acidified with 10% aq. HCl to pH 1 and diluted with DCM. The biphasic solution was separated and the aqueous layer was extracted with DCM (3×). The combined organic phase was dried over anhydrous sodium sulfate and concentrated to provide 5-(6-bromo-2-phenylquinolin-3-yl)pentanoic acid (1A, 8.97 g, LCMS (M+H)=384).

Step 2 tert-Butyl 5-(6-bromo-2-phenylquinolin-3-yl)pentanoate

1B 5-(6-Bromo-2-phenylquinolin-3-yl)pentanoic acid (1A, 4.00 g, 10.4 mmol) was dissolved in DCM (100 mL). The flask was cooled to 0° C. in an ice/water bath before TFAA (14.7 mL, 104 mmol) was slowly added. After stirring at 0° C. for 1 h, tBuOH (29.9 mL) was gradually added and the reaction mixture was allowed to warm to RT overnight. The mixture was diluted with DCM and sat. Sodium bicarbonate. The biphasic solution was separated and the aqueous layer was extracted with DCM (3×). The combined organic phase was dried over anhydrous sodium sulfate and concentrated. Chromatography (5-100% EtOAc/hexanes) afforded tert-butyl 5-(6-bromo-2-phenylquinolin-3-yl)pentanoate (1B, 3.71 g; Yield=81%, LCMS (M+H)=440).

Step 3

3-(5-tert-butoxy-5-oxopentyl)-2-phenylquinoline-6-carboxylic acid

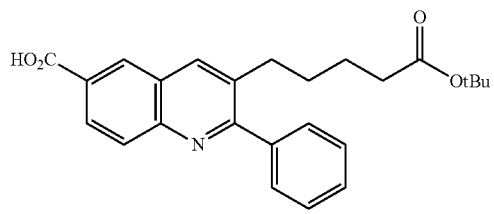

1C

Compound 1B (150 mg, 0.341 mmol), potassium carbonate (141.2 mg, 1.022 mmol), 1,3-bis(dicyclohexyl)phosphonium)propane bis(tetrafluoroborate) (229 mg, 0.375 mmol) and Pd(OAc)$_2$ (38 mg, 0.17 mmol) were dissolved in water (20 mL) and DMF (40 mL) and placed into a Parr pressure instrument. The reaction mixture was saturated with CO gas (5-6 atmospheres, ~100 psi) and was heated to 100° C. overnight. The reaction mixture was acidified with a 1N HCl solution to pH 1 and was diluted with EtOAc. The biphasic solution was separated and the organic layer was washed with brine (3×). The organic phase was concentrated and purified (5-100% EtOAc/hexanes) to provide 1C (121 mg; Yield=88%; LCMS (M+H)=406).

Step 4

5-(2-phenyl-6-(4-(trifluoromethoxy)benzylcarbamoyl)quinolin-3-yl)pentanoic acid trifluoroacetate

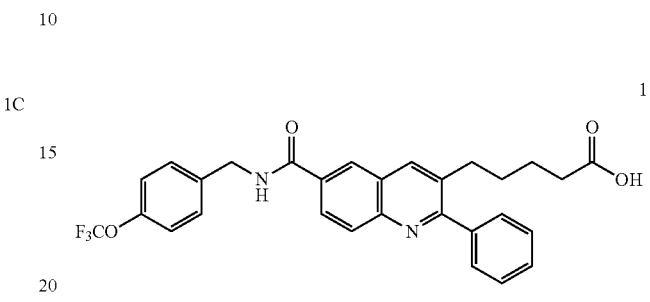

1

To a solution of 1C (51 mg, 0.126 mmol) in DCM (5 mL) was added HATU (72 mg, 0.189 mmol) followed by DIPEA (81.3 mg, 0.629 mmol) and 4-(trifluoromethoxy)benzylamine (38 uL, 0.25 mmol). The reaction mixture stirred at RT for 1 h. The reaction mixture was treated with TFA (3 mL), stirred at RT for 2 h and then concentrated to dryness under reduced pressure. Chromatography (5-100% EtOAc/hexanes) provided 1 (74 mg; Yield=92%, LCMS (M+H)=523).

In a similar manner, the following compounds were prepared by coupling acid 1C to the appropriate amine reagent followed by a TFA deprotection:

| No. | Compound | Name | M + H |
|---|---|---|---|
| 1D | | 6-[[[(3-chlorophenyl)methyl]amino]carbonyl]-2-phenyl-3-quinolinepentanoic acid | 473 |
| 1E | | 6-[[[(4-methylphenyl)methyl]amino]carbonyl]-2-phenyl-3-quinolinepentanoic acid | 453 |
| 1F | | 2-phenyl-6-[[[[4-(trifluoromethyl)phenyl]methyl]amino]carbonyl]-3-quinolinepentanoic acid | 507 |

-continued

| No. | Compound | Name | M + H |
|---|---|---|---|
| 1G | | 2-phenyl-6-[[(2,2,2-trifluoro-1(S)-phenylethyl)amino]carbonyl]-3-quinolinepentanoic acid | 507 |
| 1H | | 2-phenyl-6-[[(2,2,2-trifluoro-1(R)-phenylethyl)amino]carbonyl]-3-quinolinepentanoic acid | 507 |
| 1i | | 2-phenyl-6-[(3(S)-phenyl-1-pyrrolidinyl)carbonyl]-3-quinolinepentanoic acid | 479 |
| 1J | | 2-phenyl-6-[(3(R)-phenyl-1-pyrrolidinyl)carbonyl]-3-quinolinepentanoic acid | 479 |
| 1K | | 2-phenyl-6-[(3(S)-phenyl-1-piperidinyl)carbonyl]-3-quinolinepentanoic acid | 493 |
| 1L | | 2-phenyl-6-[(3(R)-phenyl-1-piperidinyl)carbonyl]-3-quinolinepentanoic acid | 493 |
| 1M | | 6-[[(2,3-dihydro-1H-inden-1(R)-yl)amino]carbonyl]-2-phenyl-3-quinolinepentanoic acid | 465 |

-continued

| No. | Compound | Name | M + H |
|---|---|---|---|
| 1N | | 6-[[(2,3-dihydro-1H-inden-1(S)-yl)amino]carbonyl]-2-phenyl-3-quinolinepentanoic acid | 465 |
| 1o | | 2-phenyl-6-[[(1,2,3,4-tetrahydro-1(R)-naphthalenyl)amino]carbonyl]-3-quinolinepentanoic acid | 479 |
| 1P | | 2-phenyl-6-[[(1,2,3,4-tetrahydro-1(S)-naphthalenyl)amino]carbonyl]-3-quinolinepentanoic acid | 479 |
| 1Q | | 6-[[(2,3-dihydro-1H-inden-2-yl)amino]carbonyl]-2-phenyl-3-quinolinepentanoic acid | 465 |
| 1R | | 2-phenyl-6-[(4-phenyl-1-piperidinyl)carbonyl]-3-quinolinepentanoic acid | 493 |
| 1S | | 2-phenyl-6-[[(1(R)-phenylethyl)amino]carbonyl]-3-quinolinepentanoic acid | 453 |
| 1T | | 2-phenyl-6-[[(1(S)-phenylethyl)amino]carbonyl]-3-quinolinepentanoic acid | 453 |

-continued

| No. | Compound | Name | M + H |
|---|---|---|---|
| 1U | | 6-[[methyl(phenylmethyl)amino]carbonyl]-2-phenyl-3-quinolinepentanoic acid | 453 |
| 1V | | 2-phenyl-6-[[[[6-(trifluoromethyl)-3-pyridinyl]methyl]amino]carbonyl]-3-quinolinepentanoic acid | 508 |
| 1W | | 2-phenyl-6-[[[1-(4-pyridinyl)ethyl]amino]carbonyl]-3-quinolinepentanoic acid | 454 |
| 1X | | 2-phenyl-6-[[(3-pyridinylmethyl)amino]carbonyl]-3-quinolinepentanoic acid | 440 |
| 1Y | | 2-phenyl-6-[[(4-pyridinylmethyl)amino]carbonyl]-3-quinolinepentanoic acid | 440 |
| 1Z | | 2-phenyl-6-[[[3-(1-pyrrolidinyl)propyl]amino]carbonyl]-3-quinolinepentanoic acid | 460 |
| 1AA | | 6-[[[3-(2-oxo-1-pyrrolidinyl)propyl]amino]carbonyl]-2-phenyl-3-quinolinepentanoic acid | 474 |

-continued

| No. | Compound | Name | M + H |
|---|---|---|---|
| 1AB | | 6-[(1H-indol-2-ylamino)carbonyl]-2-phenyl-3-quinolinepentanoic acid | 464 |
| 1AC | | 6-[(nonylamino)carbonyl]-2-phenyl-3-quinolinepentanoic acid | 475 |
| 1AD | | 6-[[[1(R)-(4-chlorophenyl)ethyl]amino]carbonyl]-2-phenyl-3-quinolinepentanoic acid | 487 |
| 1AE | | 6-[[[1(S)-(4-chlorophenyl)ethyl]amino]carbonyl]-2-phenyl-3-quinolinepentanoic acid | 487 |
| 1AF | | 6-[[[1(R)-(4-chlorophenyl)-2,2,2-trifluoroethyl]amino]carbonyl]-2-phenyl-3-quinolinepentanoic acid | 541 |
| 1AG | | 6-[[[1(S)-(4-chlorophenyl)-2,2,2-trifluoroethyl]amino]carbonyl]-3-phenyl-2-quinolinepentanoic acid | 541 |
| 1AH | | (R)-5-(6-((1-(4-fluorophenyl)ethyl)carbamoyl)-2-phenylquinolin-3-yl)pentanoic acid | 471 |

-continued

| No. | Compound | Name | M + H |
|---|---|---|---|
| 1Ai | | 5-(2-phenyl-6-(4-phenylpiperazine-1-carbonyl)quinolin-3-yl)pentanoic acid | 494 |
| 1AJ | | 5-(6-(3-(3-fluorophenyl)azetidine-1-carbonyl)-2-phenylquinolin-3-yl)pentanoic acid | 483 |
| 1AK | | 5-(6-((4-fluorobenzyl)(methyl)carbamoyl)-2-phenylquinolin-3-yl)pentanoic acid | 471 |
| 1AL | | (S)-5-(6-(chroman-4-ylcarbamoyl)-2-phenylquinolin-3-yl)pentanoic acid | 481 |
| 1AM | | (R)-5-(6-(3-(4-fluorophenyl)pyrrolidine-1-carbonyl)-2-phenylquinolin-3-yl)pentanoic acid | 497 |
| 1AN | | (S)-5-(6-(3-(4-fluorophenyl)pyrrolidine-1-carbonyl)-2-phenylquinolin-3-yl)pentanoic acid | 497 |
| 1Ao | | (R)-5-(6-((2,3-dihydrobenzofuran-3-yl)carbamoyl)-2-phenylquinolin-3-yl)pentanoic acid | 467 |

-continued

| No. | Compound | Name | M + H |
|---|---|---|---|
| 1AP | | 5-(6-((2,2-dimethylchroman-4-yl)carbamoyl)-2-phenylquinolin-3-yl)pentanoic acid | 509 |
| 1AQ | | 5-(6-((4,4-dimethyl-1,2,3,4-tetrahydronaphthalen-1-yl)carbamoyl)-2-phenylquinolin-3-yl)pentanoic acid | 507 |
| 1AR | | 5-(6-(3-cyano-3-phenylpyrrolidine-1-carbonyl)-2-phenylquinolin-3-yl)pentanoic acid | 504 |
| 1AS | | 5-(6-((2-oxo-1,2,3,4-tetrahydroquinolin-4-yl)carbamoyl)-2-phenylquinolin-3-yl)pentanoic acid | 494 |
| 1AT | | 5-(6-((2-(4-fluorophenyl)propan-2-yl)carbamoyl)-2-phenylquinolin-3-yl)pentanoic acid | 485 |
| 1AU | | 5-(6-(4-(2-oxo-2,3-dihydro-1H-benzo[d]imidazol-1-yl)piperidine-1-carbonyl)-2-phenylquinolin-3-yl)pentanoic acid | 549 |

-continued

| No. | Compound | Name | M + H |
|---|---|---|---|
| 1AV | | 5-(2-phenyl-6-(3H-spiro[isobenzofuran-1,4'-piperidin]-1'-ylcarbonyl)quinolin-3-yl)pentanoic acid | 521 |
| 1AW | | 5-(2-phenyl-6-(4-(pyridin-2-yl)piperazine-1-carbonyl)quinolin-3-yl)pentanoic acid | 495 |
| 1AX | | 5-(6-(4-(3-cyanopyridin-2-yl)piperazine-1-carbonyl)-2-phenylquinolin-3-yl)pentanoic acid | 520 |
| 1AY | | 5-(6-(4-(3,5-dichloropyridin-4-yl)piperazine-1-carbonyl)-2-phenylquinolin-3-yl)pentanoic acid | 563 |
| 1AZ | | 5-(6-(4-(2-cyanophenyl)piperazine-1-carbonyl)-2-phenylquinolin-3-yl)pentanoic acid | 519 |
| 1BA | | 5-(6-(4-(2-chlorophenyl)piperazine-1-carbonyl)-2-phenylquinolin-3-yl)pentanoic acid | 528 |
| 1BB | | 5-(2-phenyl-6-(4-(o-tolyl)piperazine-1-carbonyl)quinolin-3-yl)pentanoic acid | 508 |

| No. | Compound | Name | M + H |
|---|---|---|---|
| 1BC | | 5-(2-phenyl-6-(4-(m-tolyl)piperazine-1-carbonyl)quinolin-3-yl)pentanoic acid | 508 |
| 1BD | | 5-(6-(4-(4-methoxyphenyl)piperazine-1-carbonyl)-2-phenylquinolin-3-yl)pentanoic acid | 524 |
| 1BE | | 5-(6-(4-(3-methylpyridin-4-yl)piperazine-1-carbonyl)-2-phenylquinolin-3-yl)pentanoic acid | 509 |

Example 2

5-(6-(4-fluorobenzylcarbamoyl)-2-phenylquinolin-3-yl)pentanoic acid

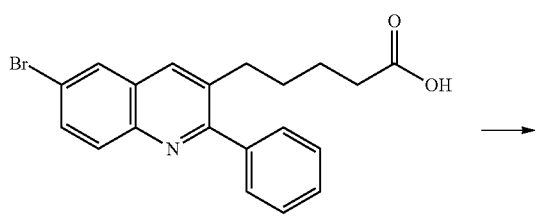

A solution of 5-(6-bromo-2-phenylquinolin-3-yl)pentanoic acid (1A, 100 mg, 0.260 mmol) in THF (4.00 mL, 49.3 mmol) in a flame dried vial under an atmosphere of nitrogen gas was treated with lithium hexamethyldisilazide (1M/THF, 780 uL). The reaction mixture stirred at RT for 10 min before it was cooled to −78° C. in an acetone/dry ice bath. A solution of nBuLi (2.5M/hexane, 229.0 uL) was slowly added and the reaction progressed for 5 minutes at −78° C. before addition of 4-fluorobenzyl isocyanate (398 uL, 3.12 mmol). The reaction was stirred at −78° C. for 20 minutes, acidified with 10% HCl to pH 1, and diluted with DCM. The biphasic solution was separated and the aqueous layer was extracted with DCM (3×). The combined organic phase was dried over anhydrous sodium sulfate, concentrated and chromatographed (5-100% EtOAc/hexanes) to provide 2 (28 mg; Yield=24%, LCMS (M+H)=439).

In a similar manner, the following compounds were prepared by reacting compound 1A with the appropriate electrophile (isocyanate or chloroformate):

| No. | Compound | Name | M + H |
|---|---|---|---|
| 2A | | 6-[[[(3-methylphenyl)methyl]amino]carbonyl]-2-phenyl-3-quinolinepentanoic acid | 453 |
| 2B | | 6-[[[(4-chlorophenyl)methyl]amino]carbonyl]-2-phenyl-3-quinolinepentanoic acid | 473 |
| 2C | | 6-[[[(4-fluorophenyl)methyl]amino]carbonyl]-2-phenyl-3-quinolinepentanoic acid | 457 |
| 2D | | 2-phenyl-6-[(phenylmethoxy)carbonyl]-3-quinolinepentanoic acid | 440 |
Example 3
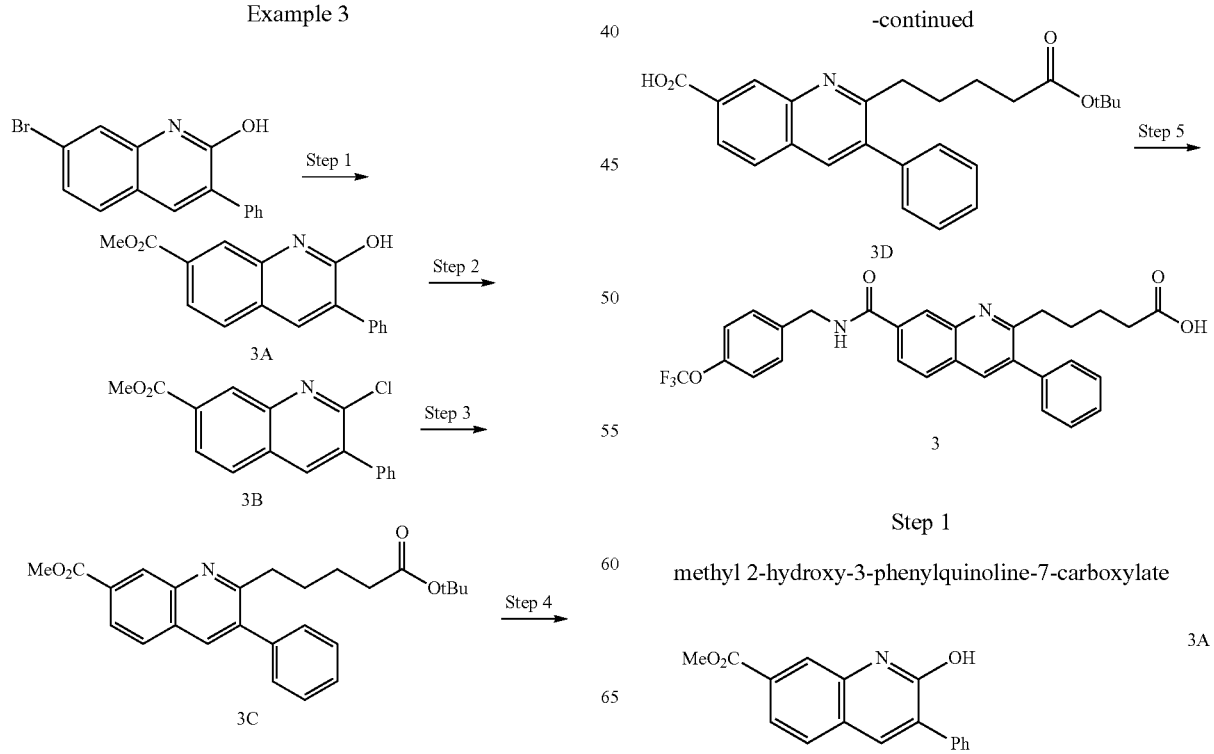
Step 1
methyl 2-hydroxy-3-phenylquinoline-7-carboxylate 7-Bromo-3-phenyl-2-quinolinol (5.00 g, 16.6 mmol), NaOAc (1.91 g, 23.3 mmol), PPh₃ (5.243 g, 19.99 mmol) and Pd(OAc)₂ (4.488 g, 20 mmol) were dissolved in MeOH (60 mL) and DMF (100 mL, 1291 mmol) and placed into a Parr pressure instrument. The reaction mixture was saturated with CO gas (5-6 atmospheres, ~100 psi) and was heated to 80° C. overnight. The reaction was concentrated and then diluted with EtOAc. The biphasic solution was separated. The organic layer was washed with brine (6×), concentrated and purified (5-100% EtOAc/hexanes) to provide 3A (methyl 2-hydroxy-3-phenylquinoline-7-carboxylate, 4.08 g; Yield=88%; LCMS (M+H)=280).

Step 2 methyl 2-chloro-3-phenylquinoline-7-carboxylate

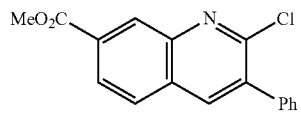
3B

A mixture of 3A (2.00 g, 7.16 mmol), SOCl₂ (30 mL, 411 mmol), and DMF (0.2 mL, 2.5 mmol) was stirred at 70° C. overnight. The mixture was concentrated to remove the excess thionyl chloride before it was diluted with DCM and water at 0° C. The biphasic solution was separated and the aqueous layer was extracted with DCM (3×). The combined organic phase was dried over anhydrous sodium sulfate and concentrated to dryness. Chromatography (5-55% EtOAc/hexanes) provided 3B (1.32 g; Yield=62%). LCMS (M+H)=298.

Step 3 methyl 2-(5-tert-butoxy-5-oxopentyl)-3-phenylquinoline-7-carboxylate

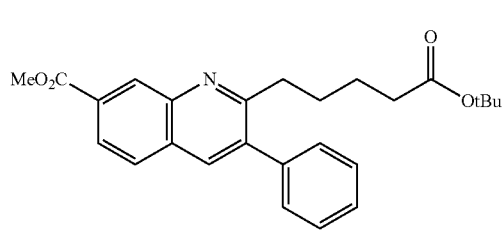
3C

To a solution of tert-butyl pent-4-enoate (0.489 g, 3.13 mmol, prepared from 4-pentenoic acid, trifluoroacetic anhydride and tBuOH) in anhydrous THF (9 mL) was added 9-BBN (0.5 M in THF, 6.260 mL). The reaction was stirred at 0° C. for 30 min and warmed to RT overnight. Compound 3B (233 mg, 0.783 mmol), Pd(dppf)Cl₂·CH₂Cl₂ (320 mg, 0.39 mmol), and K₃PO₄ (0.581 g, 2.74 mmol) were added. The suspension was degassed (3× vacuum/nitrogen) and heated at 80° C. overnight. The mixture was cooled to RT and was diluted with DCM and water. The biphasic solution was separated and the aqueous layer was extracted with DCM (3×). The combined organics were dried (Na₂SO₄), filtered, and concentrated. The residue was purified by column chromatography (5-55% EtOAc/hexane) to yield 3C (250 mg; Yield=76%). LCMS (M+H)=420.

Step 4

2-(4-carboxybutyl)-3-phenylquinoline-7-carboxylic acid

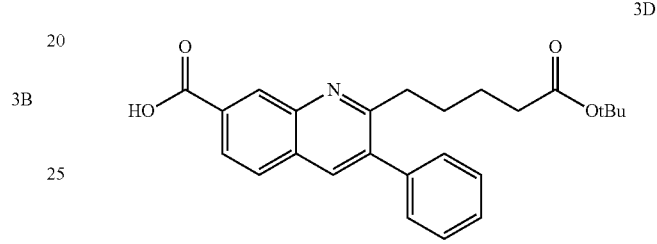
3D

A solution of 3C (400 mg, 0.954 mmol) and LiOH—H₂O (80 mg, 1.91 mmol) in THF (12 mL) and water (6 mL) was stirred at RT for 3 h. The mixture was acidified with a 10% aq. HCl to pH 1 and was diluted with DCM. The biphasic solution was separated and the aqueous layer was extracted with DCM in three portions. The combined organics were dried (Na₂SO₄), concentrated, and chromatographed (5-75% EtOAc/hex) to yield 3D (300 mg; Yield=78%; MS (M+H)=406).

Step 5

5-(3-phenyl-7-(4-(trifluoromethoxy)benzylcarbamoyl)quinolin-2-yl)pentanoic acid

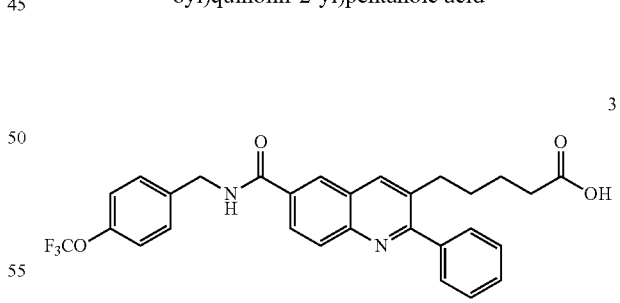
3

In a manner similar to that previously described (e.g., Example 1, Step 4), compound 3D was subjected to one-pot amide coupling with 4-(trifluoromethoxy)benzylamine and deprotection with TFA to provide the title compound 3. LCMS (M+H)=523.

In a similar manner, the following compounds were prepared by coupling acid 3D to the appropriate amine reagent followed by a TFA deprotection:

| No. | Compound | Name | M + H |
|---|---|---|---|
| 3E | | 3-phenyl-7-[(4-phenyl-1-piperidinyl)carbonyl]-2-quinolinepentanoic acid | 493 |
| 3F | | 7-[[[1(R)-(4-chlorophenyl)ethyl]amino]carbonyl]-3-phenyl-2-quinolinepentanoic acid | 487 |
| 3G | | 7-[[[1(S)-(4-chlorophenyl)ethyl]amino]carbonyl]-3-phenyl-2-quinolinepentanoic acid | 487 |
| 3H | | 3-phenyl-7-[(3(S)-phenyl-1-pyrrolidinyl)carbonyl]-2-quinolinepentanoic acid | 479 |
| 3i | | 3-phenyl-7-[(3(R)-phenyl-1-pynolidinyl)carbonyl]-2-quinolinepentanoic acid | 479 |
| 3J | | 3-phenyl-7-[(3(S)-phenyl-1-piperidinyl)carbonyl]-2-quinolinepentanoic acid | 493 |
| 3K | | 3-phenyl-7-[(3(R)-phenyl-1-piperidinyl)carbonyl]-2-quinolinepentanoic acid | 493 |

| No. | Compound | Name | M + H |
|---|---|---|---|
| 3L | 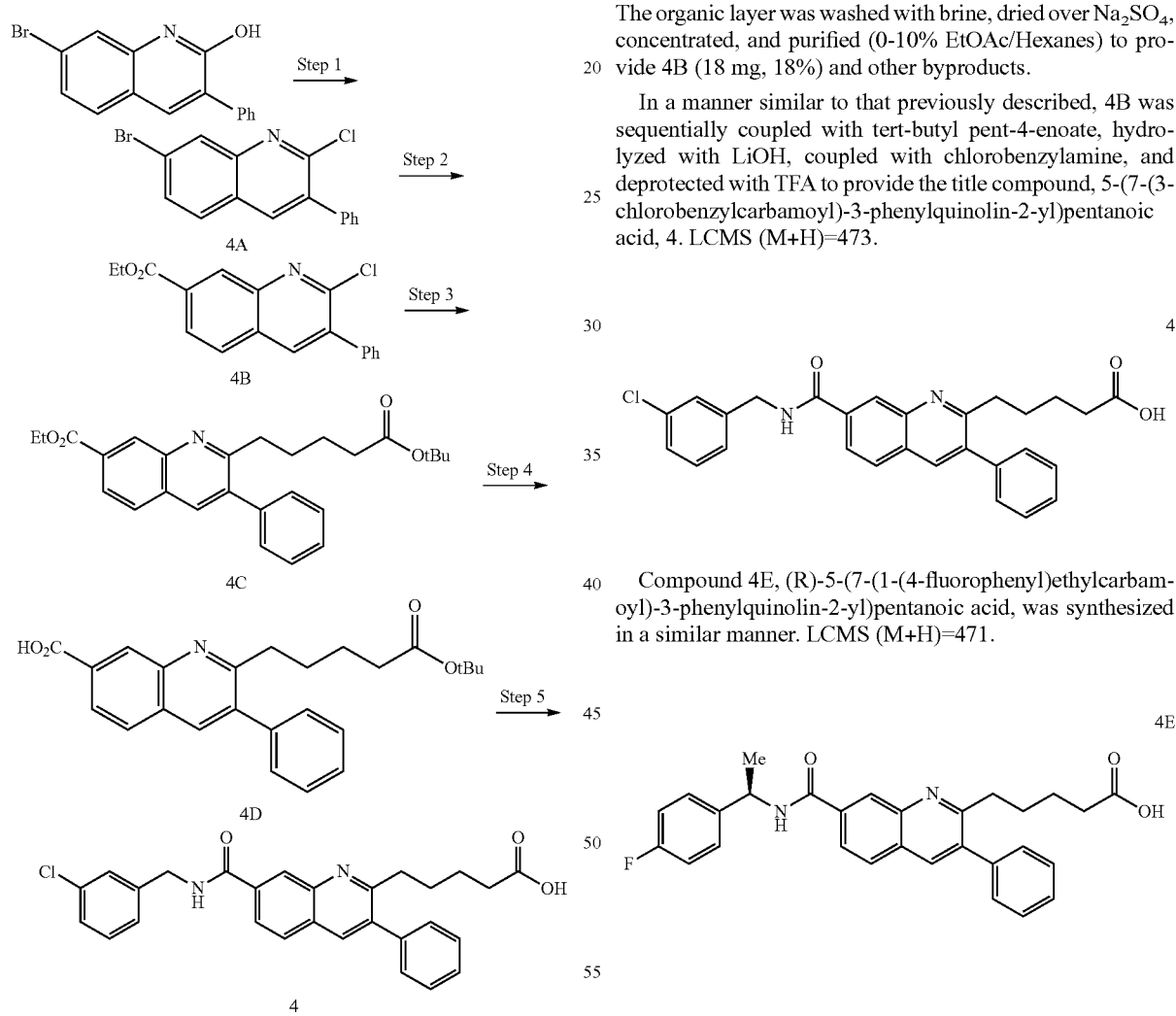 | 3-phenyl-7-[(3-phenyl-1-azetidinyl)carbonyl]-2-quinolinepentanoic acid | 465 |

Example 4

In a manner similar to that previously described, 7-bromo-3-phenyl-2-quinolinol was stirred in POCl$_3$ (110° C. overnight) to provide 4A.

nBuLi (196 µl, 0.314 mmol) was added dropwise to a chilled solution of 7-bromo-2-chloro-3-phenylquinoline (4A, 100 mg, 0.314 mmol) in THF (3.1 ml) and stirred at −78° C. for 15 min. The reaction was then quickly charged (down the side of the flask) with a solution of ethyl chloroformate (150 µl, 1.569 mmol) in THF (310 µl) and stirred at −78° C. for an additional 3 h. The reaction was quenched with sat. ammonium chloride and allowed to warm to RT. The reaction was diluted with EtOAc and water and the layers were separated. The organic layer was washed with brine, dried over Na$_2$SO$_4$, concentrated, and purified (0-10% EtOAc/Hexanes) to provide 4B (18 mg, 18%) and other byproducts.

In a manner similar to that previously described, 4B was sequentially coupled with tert-butyl pent-4-enoate, hydrolyzed with LiOH, coupled with chlorobenzylamine, and deprotected with TFA to provide the title compound, 5-(7-(3-chlorobenzylcarbamoyl)-3-phenylquinolin-2-yl)pentanoic acid, 4. LCMS (M+H)=473.

Compound 4E, (R)-5-(7-(1-(4-fluorophenyl)ethylcarbamoyl)-3-phenylquinolin-2-yl)pentanoic acid, was synthesized in a similar manner. LCMS (M+H)=471.

Example 5

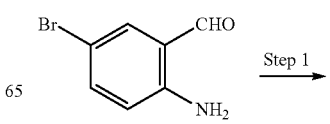

-continued

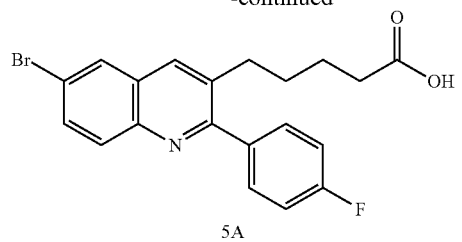

5A

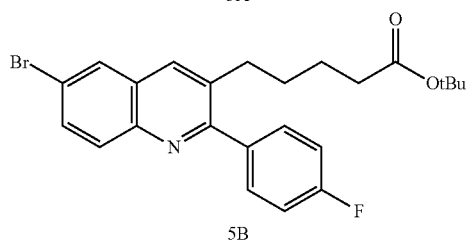

5B

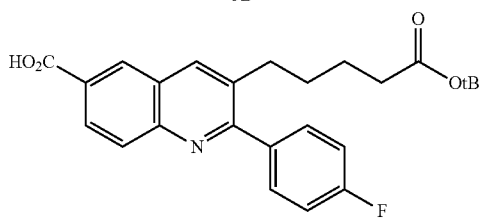

5C

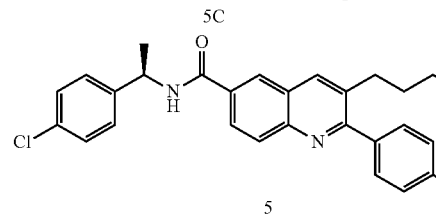

5

100° C. overnight), coupled with (R)-1-(4-chlorophenyl)ethanamine (HATU, DIPEA) and deprotected with TFA to provide the title compound, 6-[[[1(R)-(4-chlorophenyl)ethyl]amino]carbonyl]-2-(4-fluorophenyl)-3-quinolinepentanoic acid, 5. LCMS (M+H)=505.

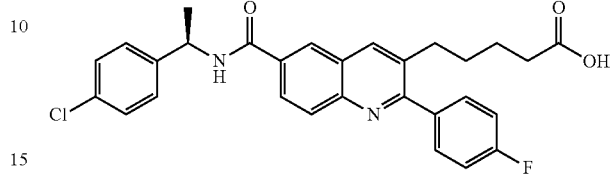

5

The t-butyl ester, intermediate 3-(5-(tert-butoxy)-5-oxopentyl)-2-(4-chlorophenyl)quinoline-6-carboxylic acid (5Z) was prepared using a similar sequence as described above by substituting 7-(4-chlorophenyl)-7-oxoheptanoic acid for 7-(4-fluorophenyl)-7-oxoheptanoic acid and by using 1 atm CO in the carboxylation step (Step 3). The intermediate carboxylic acid was coupled to appropriate amine reagents followed by TFA deprotection.

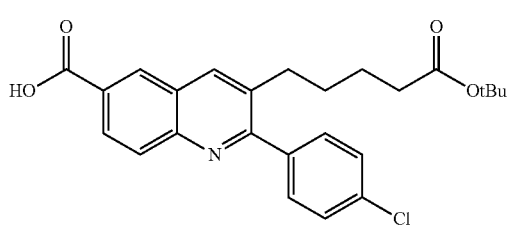

5Z

In a manner similar to that described previously (Example 1), 2-amino-5-bromobenzaldehyde was sequentially reacted with 7-(4-fluorophenyl)-7-oxoheptanoic acid and TFAA-tBuOH. The resulting ester 5B was converted to 5C (Pd(OAc)$_2$, dcpp-2(HBF)$_4$, K$_2$CO$_3$, 5 atm CO, H$_2$O-DMF, In a similar manner to the procedures described above, the following compounds were prepared by coupling acid 5C or 5Z to the appropriate amine reagent followed by a TFA deprotection:

| No. | Compound | Name | M + H |
|---|---|---|---|
| 5D | ![structure] | 2-(4-fluorophenyl)-6-[[[1(R)-(4-fluorophenyl)ethyl]amino]carbonyl]-3-quinolinepentanoic acid | 489 |
| 5E | ![structure] | 6-[[(2,3-dihydro-1H-inden-1(R)-yl)amino]carbonyl]-2-(4-fluorophenyl)-3-quinolinepentanoic acid | 483 |

-continued

| No. | Compound | Name | M + H |
|---|---|---|---|
| 5F | | 6-[[(6-fluoro-2,3-dihydro-1H-inden-1(R)-yl)amino]carbonyl]-2-(4-fluorophenyl)-3-quinolinepentanoic acid | 501 |
| 5G | | 2-(4-fluorophenyl)-6-[[(1,2,3,4-tetrahydro-1(R)-naphthalenyl)amino]carbonyl]-3-quinolinepentanoic acid | 497 |
| 5H | | 2-(4-fluorophenyl)-6-[[(7-fluoro-1,2,3,4-tetrahydro-1(R)-naphthalenyl)amino]carbonyl]-3-quinolinepentanoic acid | 515 |
| 5i | | 6-[[[1(S)-4-chlorophenyl)ethyl]amino]carbonyl]-2-(4-fluorophenyl)-3-quinolinepentanoic acid | 505 |
| 5J | | 2-(4-fluorophenyl)-6-[[[1(S)-(4-fluorophenyl)ethyl]amino]carbonyl]-3-quinolinepentanoic acid | 489 |
| 5K | | 6-[[(2,3-dihydro-1H-inden-1(S)-yl)amino]carbonyl]-2-(4-fluorophenyl)-3-quinolinepentanoic acid | 483 |

| No. | Compound | Name | M + H |
|---|---|---|---|
| 5L | | 6-[[(6-fluoro-2,3-dihydro-1H-inden-1(S)-yl)amino]carbonyl]-2-(4-fluorophenyl)-3-quinolinepentanoic acid | 501 |
| 5M | | 2-(4-fluorophenyl)-6-[[(1,2,3,4-tetrahydro-1(S)-naphthalenyl)amino]carbonyl]-3-quinolinepentanoic acid | 497 |
| 5N | | 2-(4-fluorophenyl)-6-[[(7-fluoro-1,2,3,4-tetrahydro-1(S)-naphthalenyl)amino]carbonyl]-3-quinolinepentanoic acid | 515 |
| 5o | | 6-[[(5-chloro-2,3-dihydro-1H-inden-1(R)-yl)amino]carbonyl]-2-(4-fluorophenyl)-3-quinolinepentanoic acid | 517 |
| 5P | | 6-[[(6-chloro-1,2,3,4-tetrahydro-1(R)-naphthalenyl)amino]carbonyl]-2-(4-fluorophenyl)-3-quinolinepentanoic acid | 531 |
| 5Q | | 6-[[[1(R)-(4-cyanophenyl)-2,2,2-trifluoroethyl]amino]carbonyl]-2-(4-fluorophenyl)-3-quinolinepentanoic acid | 550 |

-continued

| No. | Compound | Name | M + H |
|---|---|---|---|
| 5R | | 6-[[(5-chloro-2,3-dihydro-1H-inden-1(S)-yl)amino]carbonyl]-2-(4-fluorophenyl)-3-quinolinepentanoic acid | 517 |
| 5S | | 6-[[(6-chloro-1,2,3,4-tetrahydro-1(S)-naphthalenyl)amino]carbonyl-2-(4-fluorophenyl)-3-quinolinepentanoic acid | 531 |
| 5T | | 6-[[[1(S)-4-cyanophenyl)-2,2,2-trifluoroethyl]amino]carbonyl]-2-(4-fluorophenyl)-3-quinolinepentanoic acid | 550 |
| 5U | | 6-[[[(4-chlorophenyl)methyl]methylamino]carbonyl]-2-(4-fluorophenyl)-3-quinolinepentanoic acid | 505 |
| 5V | | 2-(4-fluorophenyl)-6-[[methyl[[4-(trifluoromethyl)phenyl]methyl]amino]carbonyl]-3-quinolinepentanoic acid | 539 |
| 5W | | 2-(4-fluorophenyl)-6-[[methyl[[3-(trifluoromethyl)phenyl]methyl]amino]carbonyl]-3-quinolinepentanoic acid | 539 |
| 5X | | 6-[[[1(R)-(3,5-dichlorophenyl)ethyl]amino]carbonyl]-2-(4-fluorophenyl)-3-quinolinepentanoic acid | 539 |

-continued

| No. | Compound | Name | M + H |
|---|---|---|---|
| 5Y | | 6-[[[1(S)-(3,5-dichlorophenyl)ethyl]amino]carbonyl]-2-(4-fluorophenyl)-3-quinolinepentanoic acid | 539 |
| 5AA | | 5-(6-(benzhydrylcarbamoyl)-2-(4-fluorophenyl)quinolin-3-yl)pentanoic acid | 533 |
| 5AB | | (R)-5-(2-(4-fluorophenyl)-6-((2-phenylpropyl)carbamoyl)quinolin-3-yl)pentanoic acid | 485 |
| 5AC | | (S)-5-(2-(4-fluorophenyl)-6-((2-phenylpropyl)carbamoyl)quinolin-3-yl)pentanoic acid | 485 |
| 5AD | | (R)-5-(6-(chroman-4-ylcarbamoyl)-2-(4-fluorophenyl)quinolin-3-yl)pentanoic acid | 499 |
| 5AE | | (R)-5-(6-((6-fluoro-1,2,3,4-tetrahydronaphthalen-1-yl)carbamoyl)-2-(4-fluorophenyl)quinolin-3-yl)pentanoic acid | 515 |

-continued

| No. | Compound | Name | M + H |
|---|---|---|---|
| 5AF | | 5-(2-(4-fluorophenyl)-6-(4-phenylpiperazine-1-carbonyl)quinolin-3-yl)pentanoic acid | 512 |
| 5AG | | 5-(2-(4-fluorophenyl)-6-(3-(3-fluorophenyl)azetidine-1-carbonyl)quinolin-3-yl)pentanoic acid | 501 |
| 5AH | | (S)-5-(2-(4-fluorophenyl)-6-(3-phenylpyrrolidine-1-carbonyl)quinolin-3-yl)pentanoic acid | 497 |
| 5Ai | | 5-(6-((4-fluorobenzyl)(methyl)carbamoyl)-2-(4-fluorophenyl)quinolin-3-yl)pentanoic acid | 489 |
| 5AJ | | 5-(6-((2,2-dimethylchroman-4-yl)carbamoyl)-2-(4-fluorophenyl)quinolin-3-yl)pentanoic acid | 527 |
| 5AK | | 5-(6-((4,4-dimethyl-1,2,3,4-tetrahydronaphthalen-1-yl)carbamoyl)-2-(4-fluorophenyl)quinolin-3-yl)pentanoic acid | 525 |

-continued

| No. | Compound | Name | M + H |
|---|---|---|---|
| 5AL | | 5-(2-(4-fluorophenyl)-6-((2-oxo-1,2,3,4-tetrahydroquinolin-4-yl)carbamoyl)quinolin-3-yl)pentanoic acid | 512 |
| 5AM | | 5-(2-(4-fluorophenyl)-6-(3-phenylazetidine-1-carbonyl)quinolin-3-yl)pentanoic acid | 483 |
| 5AN | | 5-(6-(benzylcarbamoyl)-2-(4-fluorophenyl)quinolin-3-yl)pentanoic acid | 457 |
| 5Ao | | 5-(6-(4-(2-cyanophenyl)piperazine-1-carbonyl)-2-(4-fluorophenyl)quinolin-3-yl)pentanoic acid | 537 |
| 5AP | | 5-(2-(4-fluorophenyl)-6-(4-(2-methoxyphenyl)piperidine-1-carbonyl)quinolin-3-yl)pentanoic acid | 541 |
| 5AQ | | 5-(2-(4-fluorophenyl)-6-(3H-spiro[isobenzofuran-1,4'-piperidin]-1'-ylcarbonyl)quinolin-3-yl)pentanoic acid | 539 |

-continued

| No. | Compound | Name | M + H |
|---|---|---|---|
| 5AR | | 5-(2-(4-fluorophenyl)-6-(4-(2-(trifluoromethyl)phenyl)piperazine-1-carbonyl)quinolin-3-yl)pentanoic acid | 580 |
| 5AS | | 5-(6-(4-(2-chlorophenyl)piperazine-1-carbonyl)-2-(4-fluorophenyl)quinolin-3-yl)pentanoic acid | 546 |
| 5AT | | 5-(2-(4-fluorophenyl)-6-(4-(o-tolyl)piperazine-1-carbonyl)quinolin-3-yl)pentanoic acid | 526 |
| 5AU | | 5-(2-(4-fluorophenyl)-6-(4-(m-tolyl)piperazine-1-carbonyl)quinolin-3-yl)pentanoic acid | 526 |
| 5AV | | 5-(2-(4-fluorophenyl)-6-(4-(4-methoxyphenyl)piperazine-1-carbonyl)quinolin-3-yl)pentanoic acid | 542 |
| 5AW | | 5-(2-(4-fluorophenyl)-6-(4-(p-tolyl)piperazine-1-carbonyl)quinolin-3-yl)pentanoic acid | 526 |
| 5AX | | 5-(2-(4-fluorophenyl)-6-(4-(4-fluorophenyl)piperazine-1-carbonyl)quinolin-3-yl)pentanoic acid | 530 |

| No. | Compound | Name | M + H |
|---|---|---|---|
| 5AY | | (R)-5-(2-(4-chlorophenyl)-6-((6-fluoro-1,2,3,4-tetrahydronaphthalen-1-yl)carbamoyl)quinolin-3-yl)pentanoic acid | 531 |
| 5AZ | | (R)-5-(2-(4-chlorophenyl)-6-((1,2,3,4-tetrahydronaphthalen-1-yl)carbamoyl)quinolin-3-yl)pentanoic acid | 513 |
| 5BA | | (R)-5-(2-(4-chlorophenyl)-6-(chroman-4-ylcarbamoyl)quinolin-3-yl)pentanoic acid | 515 |
| 5BB | | (S)-5-(2-(4-chlorophenyl)-6-((2,3-dihydrobenzofuran-3-yl)carbamoyl)quinolin-3-yl)pentanoic acid | 501 |
| 5BC | | (R)-5-(2-(4-chlorophenyl)-6-((1-(4-fluorophenyl)ethyl)carbamoyl)quinolin-3-yl)pentanoic acid | 505 |
| 5BD | | 5-(2-(4-chlorophenyl)-6-(4-phenylpiperazine-1-carbonyl)quinolin-3-yl)pentanoic acid | 528 |

-continued

| No. | Compound | Name | M + H |
|---|---|---|---|
| 5BE | | 5-(2-(4-chlorophenyl)-6-(3-(3-fluorophenyl)azetidine-1-carbonyl)quinolin-3-yl)pentanoic acid | 517 |
| 5BF | | (S)-5-(2-(4-chlorophenyl)-6-(3-phenylpyrrolidine-1-carbonyl)quinolin-3-yl)pentanoic acid | 513 |
| 5BG | | 5-(2-(4-chlorophenyl)-6-((4-fluorobenzyl)(methyl)carbamoyl)quinolin-3-yl)pentanoic acid | 505 |
| 5BH | | 5-(2-(4-chlorophenyl)-6-((2,2-dimethylchroman-4-yl)carbamoyl)quinolin-3-yl)pentanoic acid | 543 |
| 5Bi | | 5-(2-(4-chlorophenyl)-6-((4,4-dimethyl-1,2,3,4-tetrahydronaphthalen-1-yl)carbamoyl)quinolin-3-yl)pentanoic acid | 541 |
| 5BJ | | 5-(2-(4-chlorophenyl)-6-((2-oxo-1,2,3,4-tetrahydroquinolin-4-yl)carbamoyl)quinolin-3-yl)pentanoic acid | 528 |

| No. | Compound | Name | M + H |
|---|---|---|---|
| 5BK | | 5-(2-(4-chlorophenyl)-6-(3-phenylazetidine-1-carbonyl)quinolin-3-yl)pentanoic acid | 499 |
| 5BL | | 5-(6-(benzylcarbamoyl)-2-(4-chlorophenyl)quinolin-3-yl)pentanoic acid | 473 |
| 5BM | | 5-(2-(4-chlorophenyl)-6-(4-(2-cyanophenyl)piperazine-1-carbonyl)quinolin-3-yl)pentanoic acid | 553 |
| 5BN | | 5-(2-(4-chlorophenyl)-6-(4-(2-methoxyphenyl)piperidine-1-carbonyl)quinolin-3-yl)pentanoic acid | 557 |
| 5Bo | | 5-(2-(4-chlorophenyl)-6-(3H-spiro[isobenzofuran-1,4'-piperidin]-1'-ylcarbonyl)quinolin-3-yl)pentanoic acid | 555 |
| 5BP | | 5-(2-(4-chlorophenyl)-6-(4-(2-chlorophenyl)piperazine-1-carbonyl)quinolin-3-yl)pentanoic acid | 562 |
| 5BQ | | 5-(2-(4-chlorophenyl)-6-(4-(o-tolyl)piperazine-1-carbonyl)quinolin-3-yl)pentanoic acid | 542 |

-continued

| No. | Compound | Name | M + H |
|---|---|---|---|
| 5BR | | 5-(2-(4-chlorophenyl)-6-(4-(m-tolyl)piperazine-1-carbonyl)quinolin-3-yl)pentanoic acid | 542 |
| 5BS | | 5-(2-(4-chlorophenyl)-6-(4-(4-methoxyphenyl)piperazine-1-carbonyl)quinolin-3-yl)pentanoic acid | 558 |
| 5BT | | 5-(2-(4-chlorophenyl)-6-(4-(p-tolyl)piperazine-1-carbonyl)quinolin-3-yl)pentanoic acid | 543 |
| 5BU | | 5-(2-(4-chlorophenyl)-6-(4-(4-fluorophenyl)piperazine-1-carbonyl)quinolin-3-yl)pentanoic acid | 546 |

Preparative Example 6

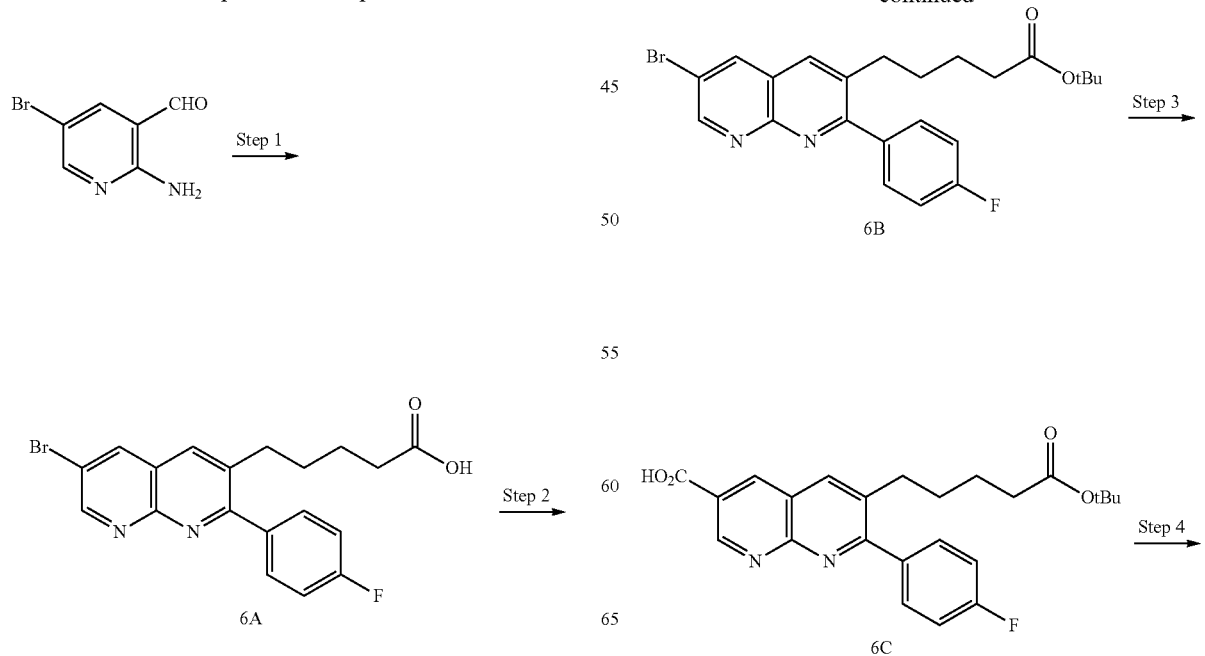

-continued

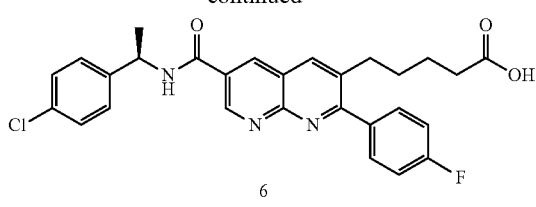

6

In a manner similar to that described previously (Example 1), 2-amino-5-bromopyridine-3-carboxaldehyde was sequentially reacted with 7-(4-fluorophenyl)-7-oxoheptanoic acid and TFAA-tBuOH. The resulting ester 6B was converted to 6C, coupled with (R)-1-(4-chlorophenyl)ethanamine, and deprotected with TFA to provide the title compound, 6-[[[1 (R)-(4-chlorophenyl)ethyl]amino]carbonyl]-2-(4-fluorophenyl)-1,8-naphthyridine-3-pentanoic acid, 6. LCMS (M+H)= 506.

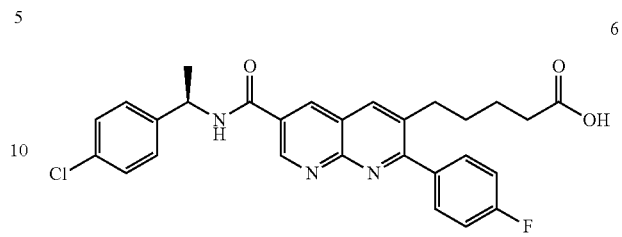

6

In a similar manner, the following compounds were prepared by coupling acid 6D to the appropriate amine reagent followed by a TFA deprotection:

| No. | Compound | Name | M + H |
|---|---|---|---|
| 6D | 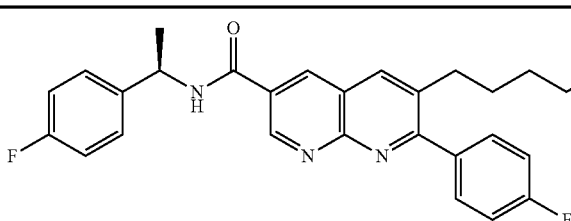 | 2-(4-fluorophenyl)-6-[[[1(R)-(4-fluorophenyl)ethyl]amino]carbonyl]-1,8-naphthyridine-3-pentanoic acid | 490 |
| 6E | 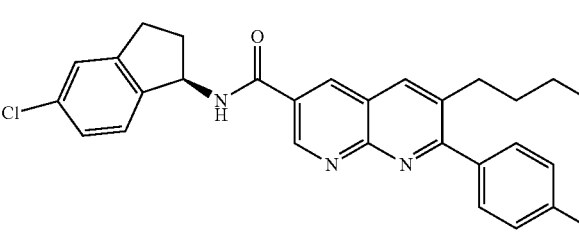 | 6-[[(5-chloro-2,3-dihydro-1H-inden-1(R)-yl)amino]carbonyl]-2-(4-fluorophenyl)-1,8-naphthyridine-3-pentanoic acid | 518 |
| 6F | 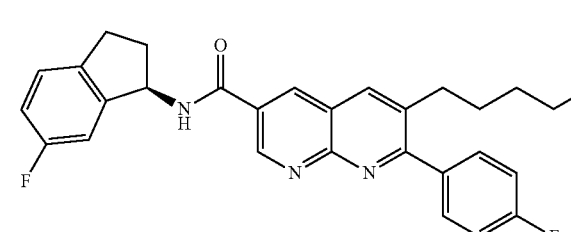 | 6-[[(6-fluoro-2,3-dihydro-1H-inden-1(R)-yl)amino]carbonyl]-2-(4-fluorophenyl)-1,8-naphthyridine-3-pentanoic acid | 502 |
| 6G | 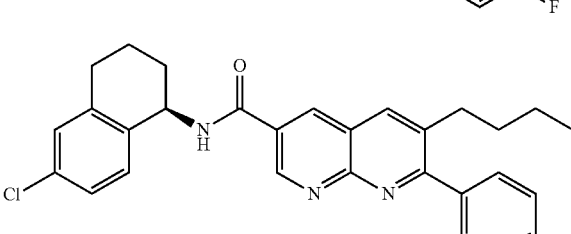 | 6-[[(6-chloro-1,2,3,4-tetrahydro-1(R)-naphthalenyl)amino)carbonyl]-2-(4-fluorophenyl)-1,8-naphthyridine-3-pentanoic acid | 532 |
| 6H | 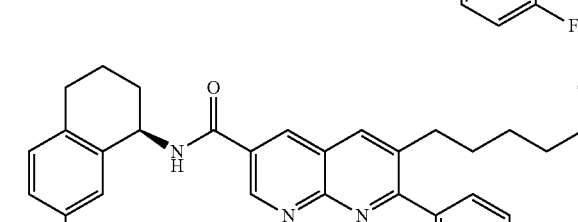 | 2-(4-fluorophenyl)-6-[[(7-fluoro-1,2,3,4-tetrahydro-1(R)-naphthalenyl)amino]carbonyl]-1,8-naphthyridine-3-pentanoic acid | 516 |

-continued

| No. | Compound | Name | M + H |
|---|---|---|---|
| 6i | | 2-(4-fluorophenyl)-6-[[[2,2,2-trifluoro-1(R)-(4-methoxyphenyl)ethyl]amino]carbonyl]-1,8-naphthyridine-3-pentanoic acid | 556 |
| 6J | | 6-[[[1(S)-(4-chlorophenyl)ethyl]amino]carbonyl]-2-(4-fluorophenyl)-1,8-naphthyridine-3-pentanoic acid | 506 |
| 6K | | 2-(4-fluorophenyl)-6-[[[1(S)-(4-fluorophenyl)ethyl]amino]carbonyl]-1,8-naphthyridine-3-pentanoic acid | 490 |
| 6L | | 6-[[(5-chloro-2,3-dihydro-1H-inden-1(S)-yl)amino]carbonyl]-2-(4-fluorophenyl)-1,8-naphthyridine-3-pentanoic acid | 518 |
| 6M | | 6-[[(6-fluoro-2,3-dihydro-1H-inden-1(S)-yl)amino]carbonyl]-2-(4-fluorophenyl)-1,8-naphthyridine-3-pentanoic acid | 502 |
| 6N | | 6-[[(6-chloro-1,2,3,4-tetrahydro-1(S)-naphthalenyl)amino]carbonyl]-2-(4-fluorophenyl)-1,8-naphthyridine-3-pentanoic acid | 532 |

-continued

| No. | Compound | Name | M + H |
|---|---|---|---|
| 6o | | 2-(4-fluorophenyl)-6-[[(7-fluoro-1,2,3,4-tetrahydro-1(S)-naphthalenyl)amino]carbonyl]-1,8-naphthyridine-3-pentanoic acid | 516 |
| 6P | | 2-(4-fluorophenyl)-6-[[[2,2,2-trifluoro-1(S)-(4-methoxyphenyl)ethyl]amino]carbonyl]-1,8-naphthyridine-3-pentanoic acid | 556 |
| 6Q | | 6-[[[1(R)-(3,5-dichlorophenyl)-2,2,2-trifluoroethyl]amino]carbonyl]-2-(4-fluorophenyl)-1,8-naphthyridine-3-pentanoic acid | 594 |
| 6R | | 6-[[[1(S)-(3,5-dichlorophenyl)-2,2,2-trifluoroethyl]amino]carbonyl]-2-(4-fluorophenyl)-1,8-naphthyridine-3-pentanoic acid | 594 |

Biological Assays

Radioligand Binding Assay A

Radioligand binding assays were performed at room temperature in 50 mM Tris-HCl pH 7.4, 1 mM EDTA containing 2 mM $MnCl_2$ and 3.0 nM [$^3$H]$PGD_2$ (New England Nuclear, Boston, Mass.) (171 Ci $mmol^{-1}$), in a final volume of 0.2 ml. Competing ligands were diluted in dimethylsulfoxide ($Me_2SO$) that was kept constant at 1% (v/v) of the final incubation volume. The reaction was initiated by the addition of 8-20 µg of membrane protein prepared from a human embryonic kidney (HEK)-$hCRTH_2$ cell line. Total and non-specific binding were determined in the absence and the presence of 10 µM $PGD_2$, respectively. Under these conditions, specific binding (total minus non-specific) of the radioligand to the receptor reached equilibrium within 50 min and was stable up to 180 min. The reaction was routinely conducted for 60 min at room temperature and terminated by rapid filtration through prewetted (0.3% polyethyleneimine) 96-well printed Filtermate™ (Wallac) using a Tomtec® harvester (Hamden, Conn.). After washing with cold buffer, the filter was dried for 2 minutes in microwave, and Meltilex Scintillator sheet (Wallac) was melted on for 2 min. The radioactivity was measured with Betaplate model 1205 (Wallac). Table A below lists representative compounds of the invention with binding data which were tested in Radioligand Binding Assay A, whereby the Ki values are rated "A", "B," "C," or "D." The Ki values are rated "A" for Ki values in the range of 0.1 to 2.0 nM, "B" for Ki values in the range from 2.1-20 nM, "C" for Ki values in the range from 20.1-200 nM, and "D" for Ki values in the range from 201-700 nM.

TABLE A

| No. | Ki (nM) |
|---|---|
| 1 | B |
| 1D | B |
| 1E | B |
| 1F | B |
| 1G | B |
| 1H | B |
| 1i | B |
| 1J | B |
| 1K | B |
| 1L | B |
| 1M | B |
| 1N | B |
| 1o | B |
| 1P | B |
| 1Q | B |
| 1R | A |
| 1S | B |
| 1T | B |

TABLE A-continued

| No. | Ki (nM) |
|-----|---------|
| 1U | B |
| 1V | B |
| 1W | C |
| 1X | C |
| 1Y | C |
| 1Z | D |
| 1AA | B |
| 1AB | B |
| 1AC | B |
| 1AD | B |
| 1AE | B |
| 1AF | B |
| 1AG | B |
| 2 | B |
| 2A | B |
| 2B | B |
| 2C | B |
| 2D | A |
| 3 | B |
| 3E | B |
| 3F | A |
| 3G | B |
| 3H | B |
| 3i | B |
| 3J | C |
| 3K | B |
| 3L | A |
| 4 | A |
| 4E | A |
| 5 | B |
| 5D | B |
| 5E | B |
| 5F | B |
| 5G | B |
| 5H | B |
| 5i | B |
| 5J | B |
| 5K | B |
| 5L | B |
| 5M | B |
| 5N | C |
| 5o | B |
| 5P | B |
| 5Q | B |
| 5R | B |
| 5S | B |
| 5T | C |
| 5U | B |
| 5V | B |
| 5W | C |
| 5X | B |
| 5Y | B |
| 5AA | B |
| 5AB | B |
| 5AC | B |
| 6 | C |
| 6D | C |
| 6E | B |
| 6F | C |
| 6G | B |
| 6H | C |
| 6i | C |
| 6J | C |
| 6K | C |
| 6L | B |
| 6M | C |
| 6N | C |
| 6o | C |
| 6P | C |
| 6Q | B |
| 6R | B |

Representative compounds of the invention had the Ki values specified in parentheses immediately following the compound number in the above-described assay: 1E (4.4 nM), 1M (3.8 nM), 1R (1.8 nM), 1X (28.9 nM), 1Z (570 nM), 1AD (3.5 nM), 3H (2.7 nM), 5F (13.6 nM), 5G (2.6 nM), 4 (0.7 mM), 5o (2.7 nM), 5N (25.5 nM), 5X (5.4 nM), 6G (6.3 nM), and 6H (160.9 nM).

Radioligand Binding Assay B

Radioligand binding also was performed using scintillation proximity assay (SPA) technology in a similar way as described above in Radioligand Binding Assay A with minor modification. Assays were done at room temperature in 10 mM HEPES pH 7.4, 1 mM EDTA containing 2 mM $MnCl_2$ and 16 nM [$^3$H]-$PGD_2$ (PerkinElmer, Waltham, Mass.) (164 Ci mmol$^{-1}$), in a final volume of 0.05 mL. Competing ligands were diluted in dimethylsulfoxide ($Me_2SO$) and added using very low volumes (50 nL). The reaction was initiated by the addition of a mixture of 3.52 μg of membrane protein prepared from a human embryonic kidney (HEK)-h$CRTH_2$ cell line adhered to 140 ug of wheatgerm agglutinin SPA beads (PerkinElmer). Total and non-specific binding were determined in the absence and the presence of 10 μM of a $CRTH_2$ antagonist, respectively. The reaction was routinely conducted for 60 min at room temperature followed by centrifugation for 5 minutes at 1000 RPM. The radioactivity was measured with a TopCountNXT (PerkinElmer). Results determined using the SPA-based assay were similar to those from the filtration binding assay.

Table B below lists representative compounds of the invention with binding data which were tested in Radioligand Binding Assay B, whereby the Ki values are rated "A", "B," "C," or "D." The Ki values are rated "A" for Ki values in the range of 0.1 to 2.0 nM, "B" for Ki values in the range from 2.1-20 nM, "C" for Ki values in the range from 20.1-200 nM, and "D" for Ki values in the range from 201-700 nM.

TABLE B

| No. | Ki (nM) |
|-----|---------|
| 1AH | C |
| 1Ai | B |
| 1AJ | B |
| 1AK | C |
| 1AL | C |
| 1AM | C |
| 1AN | B |
| 1Ao | C |
| 1AP | C |
| 1AQ | B |
| 1AR | B |
| 1AS | B |
| 1AT | C |
| 1AU | C |
| 1AV | B |
| 1AW | C |
| 1AX | C |
| 1AY | B |
| 1AZ | B |
| 1BA | B |
| 1BB | B |
| 1BC | B |
| 1BD | B |
| 2AB | C |
| 5AD | B |
| 5AE | B |
| 5AF | B |
| 5AG | C |
| 5AH | B |
| 5Ai | B |
| 5AJ | B |
| 5AK | B |
| 5AL | B |
| 5AM | B |
| 5AN | C |
| 5Ao | B |
| 5AP | B |
| 5AQ | B |

TABLE B-continued

| No. | Ki (nM) |
| --- | --- |
| 5AR | B |
| 5AS | B |
| 5AT | B |
| 5AU | B |
| 5AV | B |
| 5AW | B |
| 5AX | B |
| 5AY | B |
| 5AZ | B |
| 5BA | B |
| 5BB | B |
| 5BC | B |
| 5BD | B |
| 5BE | B |
| 5BF | B |
| 5BG | B |
| 5BH | C |
| 5Bi | B |
| 5BJ | B |
| 5BK | B |
| 5BL | B |
| 5BM | B |
| 5BN | B |
| 5Bo | B |
| 5BP | C |
| 5BQ | B |
| 5BR | B |
| 5BS | B |
| 5BT | B |
| 5BU | B |

Representative compounds of the invention had the Ki values specified in parentheses immediately following the compound number in the above-described assay: 1AL (22.3 nM), 1AY (14.0 nM), 5AF (11.6 nM), 5AT (7.2 nM), 5BH (27.3 nM), and 5BR (7.4 nM).

i[cAMP] Measurements.

The ability of the compounds to antagonize the formation of cAMP can be assayed using the ELISA-based assay described in this example. HEK-h$CRTH_2$ cells are grown to 80-90% confluency. On the day of the assay, the cells are washed with phosphate buffered saline (PBS), incubated for 2 min in cell dissociation buffer, harvested by centrifugation at 300 g for 7 min at room temperature and resuspended at 1.25e10$^6$ cells ml$^{-1}$ in Hanks' balanced salt solution containing 20 mM HEPES pH 7.4 and 0.75 mM IBMX (HBSS/HEPES/IBMX). The assay is performed in 384-plate format with 0.01 ml HBSS/HEPES/IBMX per well containing 12 500 cells and 70 to 75 nl of the test compound and DK-$PGD_2$ at various concentrations. Following a 0 to 10 to min pre-incubation of the cells with the test compound at 37° C., 0.005 ml of 30 µM Forskolin dilute in HBSS 20 mM HEPES, is added at a final concentration of 10 uM to initiate the reaction. After 10 to 60 min incubation at room temperature or 37° C., the cAMP content was quantified using the cAMP XS+HitHunter chemiluminescence assay (GE Healthcare 90-0075). Percent inhibition is calculated using the Forskolin and EC85 DK-$PGD_2$ controls.

β-Arrestin Assay:

CHO-K1 cells obtained from DiscoverX are stably transfected with human $CRTH_2$ (propagation medium: F-12, 10% FBS, 300 ug/mL hygB and 800 ug/mL G418). Cells are grown in T175 cm$^2$ flask. While in log phase, cells are collected via 0.05% trypsin treatment. Triturated cells are filtered and 40 uL (10K cells) are plated per well in a 384-well white clear bottom plate and incubated 0/N. Cell plate is emptied via inversion and blotted dry. Each well is filled with 35 uL of HBSS (with Ca$^{++}$ and Mg$^{++}$) and incubated for 5 min. Compounds are added in volumes of 1 µL and the plate is gently shaken for 2 min., followed by incubation at 37° C. for 20 min. All compounds and controls are diluted in HBSS assay buffer (with Ca$^{++}$ and Mg$^{++}$) with a final concentration range of 10$^{-5}$M to 3×10$^{-11}$ M, 11 point Dose response curves at appropriate half-log increments. Final DMSO % is ≤0.3%. Agonist Assay: 1 µl/well of compound is added into cell plate and left to incubate at 37° C. for 90 min Antagonist Assay: 1 µl/well of compounds are added into a cell plate. Incubate 30 minutes at 37° C. Stimulate cells with 1 ul/well of $PGD_2$ [100 nM] final. Incubate plate for 60 minutes at 37° C. Resulting luminescent signal is detected via Discoverx PathHunter Detection Kit per manufacturer's instructions. A total of 12 µl/well is added to each well. The plate is covered and incubated for 60 min. with gentle shaking. Chemiluminescent detection is done by a SpectraMax plate reader.

Eosinophil Shape Change Assay in Human Whole Blood:

Blood is collected in vacutainers containing EDTA. The antagonist is added to blood and incubated for 10 min at room temperature. DK-$PGD_2$ (13,14-dihydro-15-keto prostaglandin $D_2$) are then added to blood for 4 min at 37° C. in a running water bath. Blood cells are then fixed in presence of cold 0.25% (v/v) paraformaldehyde prepared in 75% (v/v) DPBS without Ca$^{++}$ and Mg$^{++}$ for 1 min on ice. 175 µL of fixed blood is transferred into 870 µL of cold 155 mM $NH_4Cl$ lysis solution and incubated at 4° C. for at least 40 min. The solution is then centrifuged at 430 g for 5 min and the supernatant is discarded. Centrifuged cells are resuspended in residual supernatant and sodium azide is added (1% final concentration). Samples are analyzed with a FACs Calibur flow cytometer (Becton Dickinson). Flow cytometry raw data is analyzed with Diva software by isolating the eosinophils from the neutrophils based on their high autofluorescence and determining the percent of total eosinophils with increased forward light scatter. Maximum (100%) and minimum (0%) shape change is determined in the presence of 10 µM DK-$PGD_2$ and DPBS, respectively. A dose response curve with DK-$PGD_2$ is performed with every assay to determine the $EC_{50}$ for each blood donor. Compounds are tested in 11-dose titration curves in the presence of 50 nM DK-$PGD_2$ to determine an antagonist $IC_{50}$.

Compounds of the present invention are selective for the $CRTH_2$ receptor over the DP receptor. Assays on the DP, as well as other prostanoid, receptors are described in WO2003106220.

While the present invention has been described in conjunction with the specific embodiments set forth above, many alternatives, modifications and other variations thereof will be apparent to those of ordinary skill in the art. All such alternatives, modifications and variations are intended to fall within the spirit and scope of the present invention.

What is claimed is:

1. A compound of the formula (IA) or a pharmaceutically acceptable salt thereof,

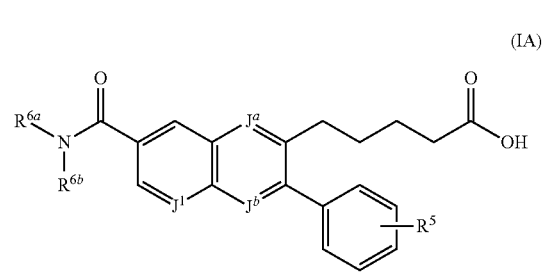

(IA)

wherein
J¹ is C(H) or N;
one of $J^a$ and $J^b$ is N, and the other is C(H);
$R^{6a}$ and $R^{6b}$ are independently:
  a. H,
  b. $C_1$-$C_{10}$ alkyl,
  c. -Q-$R^{AH}$, wherein $R^{AH}$ is selected from the group consisting of:

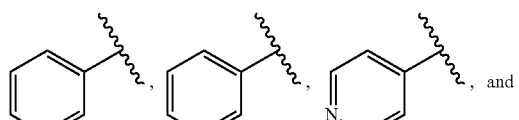

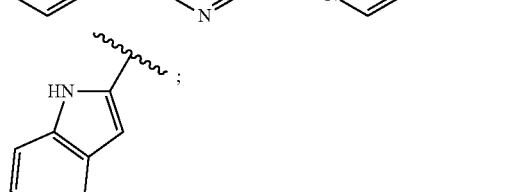

and wherein $R^{AH}$ is unsubstituted or substituted with 1 moiety selected from the group consisting of Cl, —CN, —$CH_3$, —$CF_3$, and —$OCF_3$;
Q is selected from the group consisting of a
  (i) bond;
  (ii) $C_1$-$C_3$ alkylene, wherein said alkylene is unsubstituted or substituted by one —$CH_3$, —$CF_3$, or —$CH_2CH_2OH$; and
d. -Q-$R^{HC}$, wherein
Q is as set forth in c. above;
$R^{HC}$ is selected from the group consisting of:

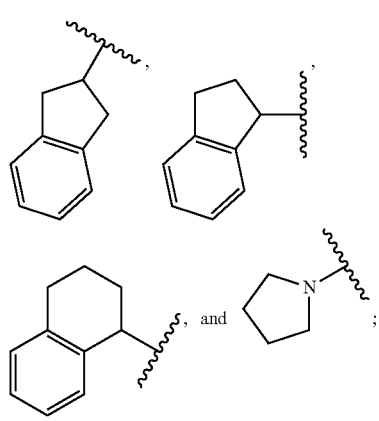

and wherein $R^{HC}$ is unsubstituted or substituted with 1 to 2 $R^{12}$ moieties independently selected from the group consisting of fluoro and chloro, or wherein when two $R^{12}$ moieties are geminally substituted on the same carbon atom, the two geminally substituted $R^{12}$ moieties, together with the carbon atom on which they are attached form —C(O)—;
e. or $R^{6a}$ and $R^{6b}$ together with the N atom to which they are attached form $R^{6H}$, wherein $R^{6H}$ is independently selected from the group consisting of:

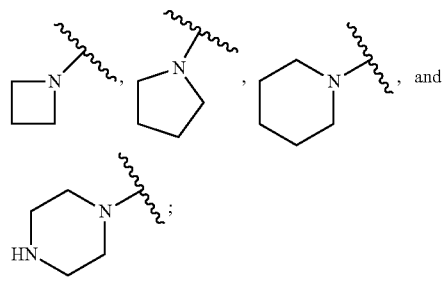

wherein $R^{6H}$ is unsubstituted or substituted by one $R^9$ moiety which is —Z—$R^{CY}$ wherein
Z is a bond; and
$R^{CY}$ is selected from the group consisting of:

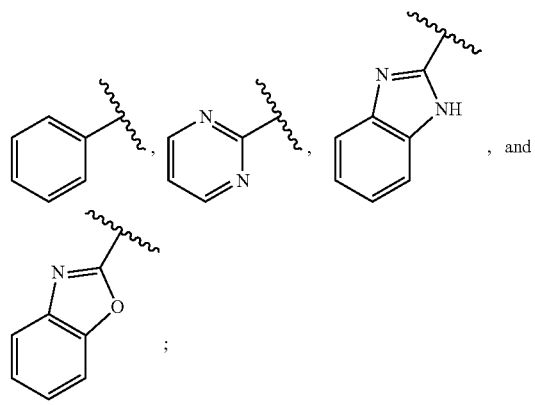

and
wherein $R^{CY}$ is unsubstituted or substituted by 1 to 2 $R^{10}$ moieties, wherein each $R^{10}$ moiety is independently selected from the group consisting of fluoro and chloro; and
$R^5$ is absent or present, and if present, is halo.

2. The compound of claim 1 or a pharmaceutically acceptable salt thereof, wherein the compound of the formula (IA) has the formula (IB)

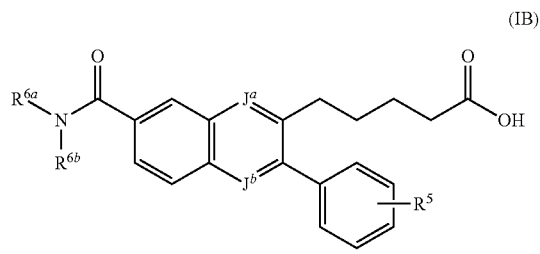

(IB)

wherein one of $J^a$ and $J^b$ is N and the other is C(H);
a) $R^{6a}$ is H and
  $R^{6b}$ is -Q-$R^{AH}$, wherein $R^{AH}$ is phenyl,
    wherein $R^{AH}$ is unsubstituted or substituted with moiety independently selected from the group consisting of fluoro, chloro, $C_1$-$C_3$ alkyl, and —O—($C_1$-$C_3$ fluoroalkyl);
  Q is methylene, wherein said methylene is unsubstituted or substituted by one $C_1$-$C_3$ alkyl or $C_1$-$C_3$ fluoroalkyl;

b) $R^{6a}$ is H and
$R^{6b}$ is -Q-$R^{HC}$, wherein
Q is as set forth in a) above;
$R^{HC}$ is selected from the group consisting of:

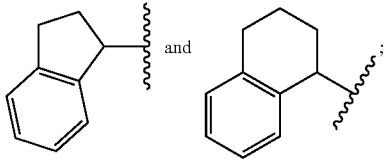 [SMILES: *C1CCc2ccccc21 ; *C1CCCc2ccccc21]

and wherein $R^{HC}$ is unsubstituted or substituted with 1 chloro;
c) or $R^{6a}$ and $R^{6b}$ together with the N atom to which they are attached form
$R^{6H}$, wherein $R^{6H}$ is

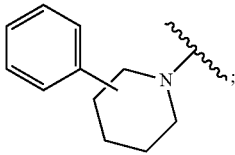

and
$R^5$ is absent or present, and if present, is fluoro.

3. The compound of claim 1 or a pharmaceutically acceptable salt thereof, wherein $J^1$ is C(H), $J^a$ is C(H) and $J^b$ is N.

4. The compound of claim 1 or a pharmaceutically acceptable salt thereof, wherein $J^1$ is C(H), $J^a$ is N and $J^b$ is C(H).

5. The compound of claim 1 or a pharmaceutically acceptable salt thereof, wherein $J^1$ is N, $J^a$ is C(H) and $J^b$ is N.

6. The compound of claim 2 or a pharmaceutically acceptable salt thereof, wherein $J^a$ is C(H) and $J^b$ is N.

7. The compound of claim 2 or a pharmaceutically acceptable salt thereof, wherein $J^a$ is N and $J^b$ is C(H).

8. A compound or a pharmaceutically acceptable salt thereof, wherein the compound is selected from the group consisting of:
   (1) 2-phenyl-6-[[[[4-(trifluoromethoxy)phenyl]methyl]amino]carbonyl]-3-quinolinepentanoic acid;
   (1D 6-[[[(3-chlorophenyl)methyl]amino]carbonyl]-2-phenyl-3-quinolinepentanoic acid;
   (1E) 6-[[[(4-methylphenyl)methyl]amino]carbonyl]-2-phenyl-3-quinolinepentanoic acid;
   (1L) 2-phenyl-6-[(3(R)-phenyl-1-piperidinyl)carbonyl]-3-quinolinepentanoic acid;
   (1T) 2-phenyl-6-[[(1(S)-phenylethyl)amino]carbonyl]-3-quinolinepentanoic acid;
   (1AD) 6-[[[1(R)-(4-chlorophenyl)ethyl]amino]carbonyl]-2-phenyl-3-quinolinepentanoic acid;
   (1AE) 6-[[[1(S)-(4-chlorophenyl)ethyl]amino]carbonyl]-2-phenyl-3-quinolinepentanoic acid;
   (1AF) 6-[[[1(R)-(4-chlorophenyl)-2,2,2-trifluoroethyl]amino]carbonyl]-2-phenyl-3-quinolinepentanoic acid;
   (1AG) 6-[[[1(S)-(4-chlorophenyl)-2,2,2-trifluoroethyl]amino]carbonyl]-3-phenyl-2-quinolinepentanoic acid;
   (1M) 6-[[(2,3-dihydro-1H-inden-1(R)-yl)amino]carbonyl]-2-phenyl-3-quinolinepentanoic acid;
   (2) 2-phenyl-6-[[(phenylmethyl)amino]carbonyl]-3-quinolinepentanoic acid;
   (2C) 6-[[[(4-fluorophenyl)methyl]amino]carbonyl]-2-phenyl-3-quinolinepentanoic acid;
   (3E) 3-phenyl-7-[(4-phenyl-1-piperidinyl)carbonyl]-2-quinolinepentanoic acid;
   (4) 5-(7-(3-chlorobenzylcarbamoyl)-3-phenylquinolin-2-yl)pentanoic acid;
   (4E) (R)-5-(7-(1-(4-fluorophenyl)ethylcarbamoyl)-3-phenylquinolin-2-yl)pentanoic acid;
   (5G) 2-(4-fluorophenyl)-6-[[(1,2,3,4-tetrahydro-1(R)-naphthalenyl)amino]carbonyl]-3-quinolinepentanoic acid;
   (5o) 6-[[[(5-chloro-2,3-dihydro-1H-inden-1(R)-yl)amino]carbonyl]-2-(4-fluorophenyl)-3-quinolinepentanoic acid; and
   (6G) 6-[[[(6-chloro-1,2,3,4-tetrahydro-1(R)-naphthalenyl)amino]carbonyl]-2-(4-fluorophenyl)-1,8-naphthyridine-3-pentanoic acid.

9. A compound or a pharmaceutically acceptable salt thereof, wherein the compound is selected from the group consisting of:
   (1AH) (R)-5-(6-((1-(4-fluorophenyl)ethyl)carbamoyl)-2-phenylquinolin-3-yl)pentanoic acid;
   (1Ai) 5-(2-phenyl-6-(4-phenylpiperazine-1-carbonyl)quinolin-3-yl)pentanoic acid;
   (1AJ) 5-(6-(3-(3-fluorophenyl)azetidine-1-carbonyl)-2-phenylquinolin-3-yl)pentanoic acid;
   (1AK) 5-(6-((4-fluorobenzyl)(methyl)carbamoyl)-2-phenylquinolin-3-yl)pentanoic acid;
   (1AL) (S)-5-(6-(chroman-4-ylcarbamoyl)-2-phenylquinolin-3-yl)pentanoic acid;
   (1AM) (R)-5-(6-(3-(4-fluorophenyl)pyrrolidine-1-carbonyl)-2-phenylquinolin-3-yl)pentanoic acid;
   (1AN) (S)-5-(6-(3-(4-fluorophenyl)pyrrolidine-1-carbonyl)-2-phenylquinolin-3-yl)pentanoic acid;
   (1Ao) (R)-5-(6-((2,3-dihydrobenzofuran-3-yl)carbamoyl)-2-phenylquinolin-3-yl)pentanoic acid;
   (1AP) 5-(6-((2,2-dimethylchroman-4-yl)carbamoyl)-2-phenylquinolin-3-yl)pentanoic acid;
   (1AQ) 5-(6-((4,4-dimethyl-1,2,3,4-tetrahydronaphthalen-1-yl)carbamoyl)-2-phenylquinolin-3-yl)pentanoic acid;
   (1AR) 5-(6-(3-cyano-3-phenylpyrrolidine-1-carbonyl)-2-phenylquinolin-3-yl)pentanoic acid;
   (1AS) 5-(6-((2-oxo-1,2,3,4-tetrahydroquinolin-4-yl)carbamoyl)-2-phenylquinolin-3-yl)pentanoic acid;
   (1AT) 5-(6-((2-(4-fluorophenyl)propan-2-yl)carbamoyl)-2-phenylquinolin-3-yl)pentanoic acid;
   (1AU) 5-(6-(4-(2-oxo-2,3-dihydro-1H-benzo[d]imidazol-1-yl)piperidine-1-carbonyl)-2-phenylquinolin-3-yl)pentanoic acid;
   (1AV) 5-(2-phenyl-6-(3H-spiro[isobenzofuran-1,4'-piperidin]-1'-ylcarbonyl)quinolin-3-yl)pentanoic acid;
   (1AW) 5-(2-phenyl-6-(4-(pyridin-2-yl)piperazine-1-carbonyl)quinolin-3-yl)pentanoic acid;
   (1AX) 5-(6-(4-(3-cyanopyridin-2-yl)piperazine-1-carbonyl)-2-phenylquinolin-3-yl)pentanoic acid;
   (1AY) 5-(6-(4-(3,5-dichloropyridin-4-yl)piperazine-1-carbonyl)-2-phenylquinolin-3-yl)pentanoic acid;
   (1AZ) 5-(6-(4-(2-cyanophenyl)piperazine-1-carbonyl)-2-phenylquinolin-3-yl)pentanoic acid;
   (1BA) 5-(6-(4-(2-chlorophenyl)piperazine-1-carbonyl)-2-phenylquinolin-3-yl)pentanoic acid;
   (1BB) 5-(2-phenyl-6-(4-(o-tolyl)piperazine-1-carbonyl)quinolin-3-yl)pentanoic acid;
   (1BC) 5-(2-phenyl-6-(4-(m-tolyl)piperazine-1-carbonyl)quinolin-3-yl)pentanoic acid;
   (1BD) 5-(6-(4-(4-methoxyphenyl)piperazine-1-carbonyl)-2-phenylquinolin-3-yl)pentanoic acid;
   (1BE) 5-(6-(4-(3-methylpyridin-4-yl)piperazine-1-carbonyl)-2-phenylquinolin-3-yl)pentanoic acid;

(5AA) 5-(6-(benzhydrylcarbamoyl)-2-(4-fluorophenyl)quinolin-3-yl)pentanoic acid;
(5AB) (R)-5-(2-(4-fluorophenyl)-6-((2-phenylpropyl)carbamoyl)quinolin-3-yl)pentanoic acid;
(5AC) (S)-5-(2-(4-fluorophenyl)-6-((2-phenylpropyl)carbamoyl)quinolin-3-yl)pentanoic acid;
(5AD) (R)-5-(6-(chroman-4-ylcarbamoyl)-2-(4-fluorophenyl)quinolin-3-yl)pentanoic acid;
(5AE) (R)-5-(6-((6-fluoro-1,2,3,4-tetrahydronaphthalen-1-yl)carbamoyl)-2-(4-fluorophenyl)quinolin-3-yl)pentanoic acid;
(5AF) 5-(2-(4-fluorophenyl)-6-(4-phenylpiperazine-1-carbonyl)quinolin-3-yl)pentanoic acid;
(5AG) 5-(2-(4-fluorophenyl)-6-(3-(3-fluorophenyl)azetidine-1-carbonyl)quinolin-3-yl)pentanoic acid;
(5AH) (S)-5-(2-(4-fluorophenyl)-6-(3-phenylpyrrolidine-1-carbonyl)quinolin-3-yl)pentanoic acid;
(5Ai) 5-(6-((4-fluorobenzyl)(methyl)carbamoyl)-2-(4-fluorophenyl)quinolin-3-yl)pentanoic acid;
(5AJ) 5-(6-((2,2-dimethylchroman-4-yl)carbamoyl)-2-(4-fluorophenyl)quinolin-3-yl)pentanoic acid;
(5AK) 5-(6-((4,4-dimethyl-1,2,3,4-tetrahydronaphthalen-1-yl)carbamoyl)-2-(4-fluorophenyl)quinolin-3-yl)pentanoic acid;
(5AL) 5-(2-(4-fluorophenyl)-6-((2-oxo-1,2,3,4-tetrahydroquinolin-4-yl)carbamoyl)quinolin-3-yl)pentanoic acid;
(5AM) 5-(2-(4-fluorophenyl)-6-(3-phenylazetidine-1-carbonyl)quinolin-3-yl)pentanoic acid;
(5AN) 5-(6-(benzylcarbamoyl)-2-(4-fluorophenyl)quinolin-3-yl)pentanoic acid;
(5Ao) 5-(6-(4-(2-cyanophenyl)piperazine-1-carbonyl)-2-(4-fluorophenyl)quinolin-3-yl)pentanoic acid;
(5AP) 5-(2-(4-fluorophenyl)-6-(4-(2-methoxyphenyl)piperidine-1-carbonyl)quinolin-3-yl)pentanoic acid;
(5AQ) 5-(2-(4-fluorophenyl)-6-(3H-spiro[isobenzofuran-1,4'-piperidin]-1'-ylcarbonyl)quinolin-3-yl)pentanoic acid;
(5AR) 5-(2-(4-fluorophenyl)-6-(4-(2-(trifluoromethyl)phenyl)piperazine-1-carbonyl)quinolin-3-yl)pentanoic acid;
(5AS) 5-(6-(4-(2-chlorophenyl)piperazine-1-carbonyl)-2-(4-fluorophenyl)quinolin-3-yl)pentanoic acid;
(5AT) 5-(2-(4-fluorophenyl)-6-(4-(o-tolyl)piperazine-1-carbonyl)quinolin-3-yl)pentanoic acid;
(5AU) 5-(2-(4-fluorophenyl)-6-(4-(m-tolyl)piperazine-1-carbonyl)quinolin-3-yl)pentanoic acid;
(5AV) 5-(2-(4-fluorophenyl)-6-(4-(4-methoxyphenyl)piperazine-1-carbonyl)quinolin-3-yl)pentanoic acid;
(5AW) 5-(2-(4-fluorophenyl)-6-(4-(p-tolyl)piperazine-1-carbonyl)quinolin-3-yl)pentanoic acid;
(5AX) 5-(2-(4-fluorophenyl)-6-(4-(4-fluorophenyl)piperazine-1-carbonyl)quinolin-3-yl)pentanoic acid;
(5AY) (R)-5-(2-(4-chlorophenyl)-6-((6-fluoro-1,2,3,4-tetrahydronaphthalen-1-yl)carbamoyl)quinolin-3-yl)pentanoic acid;
(5AZ) (R)-5-(2-(4-chlorophenyl)-6-((1,2,3,4-tetrahydronaphthalen-1-yl)carbamoyl)quinolin-3-yl)pentanoic acid;
(5BA) (R)-5-(2-(4-chlorophenyl)-6-(chroman-4-ylcarbamoyl)quinolin-3-yl)pentanoic acid;
(5BB) (S)-5-(2-(4-chlorophenyl)-6-((2,3-dihydrobenzofuran-3-yl)carbamoyl)quinolin-3-yl)pentanoic acid;
(5BC) (R)-5-(2-(4-chlorophenyl)-6-((1-(4-fluorophenyl)ethyl)carbamoyl)quinolin-3-yl)pentanoic acid;
(5BD) 5-(2-(4-chlorophenyl)-6-(4-phenylpiperazine-1-carbonyl)quinolin-3-yl)pentanoic acid;
(5BE) 5-(2-(4-chlorophenyl)-6-(3-(3-fluorophenyl)azetidine-1-carbonyl)quinolin-3-yl)pentanoic acid;
(5BF) (S)-5-(2-(4-chlorophenyl)-6-(3-phenylpyrrolidine-1-carbonyl)quinolin-3-yl)pentanoic acid;
(5BG) 5-(2-(4-chlorophenyl)-6-((4-fluorobenzyl)(methyl)carbamoyl)quinolin-3-yl)pentanoic acid;
(5BH) 5-(2-(4-chlorophenyl)-6-((2,2-dimethylchroman-4-yl)carbamoyl)quinolin-3-yl)pentanoic acid;
(5Bi) 5-(2-(4-chlorophenyl)-6-((4,4-dimethyl-1,2,3,4-tetrahydronaphthalen-1-yl)carbamoyl)quinolin-3-yl)pentanoic acid;
(5BJ) 5-(2-(4-chlorophenyl)-6-((2-oxo-1,2,3,4-tetrahydroquinolin-4-yl)carbamoyl)quinolin-3-yl)pentanoic acid;
(5BK) 5-(2-(4-chlorophenyl)-6-(3-phenylazetidine-1-carbonyl)quinolin-3-yl)pentanoic acid;
(5BL) 5-(6-(benzylcarbamoyl)-2-(4-chlorophenyl)quinolin-3-yl)pentanoic acid;
(5BM) 5-(2-(4-chlorophenyl)-6-(4-(2-cyanophenyl)piperazine-1-carbonyl)quinolin-3-yl)pentanoic acid;
(5BN) 5-(2-(4-chlorophenyl)-6-(4-(2-methoxyphenyl)piperidine-1-carbonyl)quinolin-3-yl)pentanoic acid;
(5Bo) 5-(2-(4-chlorophenyl)-6-(3H-spiro[isobenzofuran-1,4'-piperidin]-1'-ylcarbonyl)quinolin-3-yl)pentanoic acid;
(5BP) 5-(2-(4-chlorophenyl)-6-(4-(2-chlorophenyl)piperazine-1-carbonyl)quinolin-3-yl)pentanoic acid;
(5BQ) 5-(2-(4-chlorophenyl)-6-(4-(o-tolyl)piperazine-1-carbonyl)quinolin-3-yl)pentanoic acid;
(5BR) 5-(2-(4-chlorophenyl)-6-(4-(m-tolyppiperazine-1-carbonyl)quinolin-3-yl)pentanoic acid;
(5BS) 5-(2-(4-chlorophenyl)-6-(4-(4-methoxyphenyl)piperazine-1-carbonyl)quinolin-3-yl)pentanoic acid;
(5BT) 5-(2-(4-chlorophenyl)-6-(4-(p-tolyl)piperazine-1-carbonyl)quinolin-3-yl)pentanoic acid; and
(5BU) 5-(2-(4-chlorophenyl)-6-(4-(4-fluorophenyl)piperazine-1-carbonyl)quinolin-3-yl)pentanoic acid.

10. A pharmaceutical composition comprising an effective amount of the compound of claim 1, or a pharmaceutically acceptable salt thereof, and a pharmaceutically acceptable carrier.

11. A method for treating a disease or condition which is asthma, congestion, allergic rhinitis or COPD comprising administering to a patient in need of such treatment an effective amount of a compound of claim 1 or a pharmaceutically acceptable salt thereof.

12. The method of claim 11, wherein the disease or condition is asthma.

* * * * *